(12) United States Patent
Helber et al.

(10) Patent No.: US 7,544,425 B2
(45) Date of Patent: Jun. 9, 2009

(54) ORGANIC ELEMENT FOR ELECTROLUMINESCENT DEVICES

(75) Inventors: Margaret J. Helber, Webster, NY (US); Michele L. Ricks, Rochester, NY (US); Peter G. Bessey, Clifton Springs, NY (US); Tukaram K. Hatwar, Penfield, NY (US); Jeffrey P. Spindler, Rochester, NY (US); Zbyslaw R. Owczarczyk, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 721 days.

(21) Appl. No.: 11/114,383

(22) Filed: Apr. 26, 2005

(65) Prior Publication Data

US 2006/0093856 A1 May 4, 2006

Related U.S. Application Data

(63) Continuation-in-part of application No. 10/977,839, filed on Oct. 29, 2004, now abandoned.

(51) Int. Cl.
*H01L 51/54* (2006.01)
*C09K 11/06* (2006.01)
*C07C 211/54* (2006.01)

(52) U.S. Cl. .................. 428/690; 428/917; 313/504; 313/506; 564/433; 564/434; 257/40

(58) Field of Classification Search ............... 313/504, 313/506; 564/433, 434
See application file for complete search history.

(56) References Cited

U.S. PATENT DOCUMENTS

| | | | |
|---|---|---|---|
| 4,666,810 A | 5/1987 | Umehara et al. | |
| 5,121,029 A | 6/1992 | Hosokawa et al. | |
| 5,389,444 A | 2/1995 | Hosokawa et al. | |
| 5,807,627 A * | 9/1998 | Friend et al. | 428/212 |
| 5,922,481 A * | 7/1999 | Etzbach et al. | 428/690 |
| 5,935,721 A * | 8/1999 | Shi et al. | 428/690 |
| 6,534,199 B1 | 3/2003 | Hosokawa et al. | |
| 2002/0028346 A1 | 3/2002 | Shi et al. | |
| 2004/0146742 A1 | 7/2004 | Hsu et al. | |

FOREIGN PATENT DOCUMENTS

| | | | |
|---|---|---|---|
| EP | 0 557 534 | | 4/1993 |
| JP | 62-018565 | * | 1/1987 |
| JP | 62018565 | | 1/1987 |
| JP | 2004196716 | | 7/2004 |
| WO | 2004/018587 | | 3/2004 |

* cited by examiner

*Primary Examiner*—Dawn Garrett
(74) *Attorney, Agent, or Firm*—Raymond L. Owens

(57) ABSTRACT

An organic electroluminescent device comprises a cathode, an anode, and has therebetween a light-emitting layer comprising an emissive component represented by formula (I):

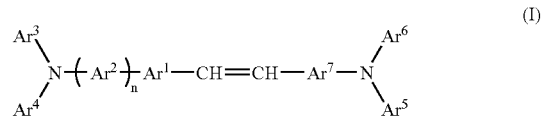

wherein:
$Ar^1$, each $Ar^2$, and $Ar^3$ through $Ar^7$ are independently selected aryl or heteroaryl groups, which may contain additional fused rings and provided that two aryl or heteroaryl rings may be joined;
n is 1, 2 or 3. The device exhibits good luminous yield with desirable color coordinates, particularly in the blue or blue-green region.

30 Claims, 2 Drawing Sheets

ORGANIC ELEMENT FOR ELECTROLUMINESCENT DEVICES

CROSS REFERENCE TO RELATED APPLICATIONS

This is a continuation-in-part of application Ser. No. 10/977,839, filed Oct. 29, 2004 (now abandoned) entitled Organic Element for Electroluminescent Devices by Margaret J. Helber, et al, which is incorporated herein by reference.

FIELD OF THE INVENTION

This invention relates to an organic light emitting diode (OLED) electroluminescent (EL) device with improved luminous yield comprising a light-emitting layer comprising a certain emissive dopant containing a 1,2-disubstituted ethylene nucleus linked through specified groups to terminal triarylamino groups.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 µm). Consequently, operating voltages were very high, often >100V.

More recent organic EL devices include an organic EL element consisting of extremely thin layers (e.g. <1.0 µm) between the anode and the cathode. Herein, the term "organic EL element" encompasses the layers between the anode and cathode. Reducing the thickness lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, and therefore, it is referred to as the hole-transporting layer, and the other organic layer is specifically chosen to transport electrons, and is referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al (J. Applied Physics, 65, Pages 3610-3616, (1989)). The light-emitting layer commonly consists of a host material doped with a guest material, also known as a dopant. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency Since these early inventions, further improvements in device materials have resulted in improved performance in attributes such as color, stability, luminous yield and manufacturability, e.g., as disclosed in U.S. Pat. Nos. 5,061,569, 5,409,783, 5,554,450, 5,593,788, 5,683,823, 5,908,581, 5,928,802, 6,020,078, and 6,208,077, amongst others.

A white-emitting electroluminescent (EL) layer can be used to form a multicolor device. Each pixel is coupled with a color filter element as part of a color filter array (CFA) to achieve a pixilated multicolor display. The organic EL layer is common to all pixels and the final color as perceived by the viewer is dictated by that pixel's corresponding color filter element. Therefore a multicolor or RGB device can be produced without requiring any patterning of the organic EL layers. An example of a white CFA top-emitting device is shown in U.S. Pat. No. 6,392,340.

White light producing OLED devices should be bright, efficient, and generally have Commission International d'Eclairage (CIE) chromaticity coordinates of about (0.33, 0.33). In any event, in accordance with this disclosure, white light is that light which is perceived by a user as having a white color. The following patents and publications disclose the preparation of organic OLED devices capable of producing white light, comprising a hole-transporting layer and an organic luminescent layer, and interposed between a pair of electrodes.

White light producing OLED devices have been reported before by J. Shi (U.S. Pat. No. 5,683,823) wherein the luminescent layer includes red and blue light-emitting materials uniformly dispersed in a host emitting material. Sato et al. in JP 07,142,169 disclose an OLED device, capable of emitting white light, made by forming a blue light-emitting layer next to the hole-transporting layer and followed by a green light-emitting layer having a region containing a red fluorescent layer.

Kido et al., in *Science*, 267, 1332 (1995) and in *Applied Physics Letters*, 64, 815 (1994), report a white light-producing OLED device. In this device, three emitter layers with different carrier transport properties, each emitting blue, green, or red light, are used to generate white light. Littman et al. in U.S. Pat. No. 5,405,709 disclose another white emitting device, which is capable of emitting white light in response to hole-electron recombination, and comprises a fluorescent in a visible light range from bluish green to red. More recently, Deshpande et al., in *Applied Physics Letters*, 75, 888 (1999), published a white OLED device using red, blue, and green luminescent layers separated by a hole-blocking layer.

Notwithstanding these developments, there are continuing needs for organic EL device components, such as light-emitting materials, sometimes referred to as dopants, that will provide high luminance efficiencies combined with high color purity and long lifetimes. In particular, there is a need to be able to adjust the emission wavelength of the light-emitting material for various applications. For example, efficient emissive blue dopants continue to be of significant interest. Emissive blue dopants containing the perylene nucleus (S. A. Van Slyke, U.S. Pat. No. 5,151,629) have been employed commercially for a number of years. For example, a perylene derivative, (2,5,8,11)-tetra-tert-butylperylene (TBP), has been used commercially in part because of its desirable CIE color coordinates (JP 09-241629). In addition to perylenes, emissive blue dopants containing one or more stilbene structures have been described (U.S. Pat. No. 5,121,029, EP 373, 582, U.S. Pat. Nos. 2,651,237, 2,670,121, 2,774,654, 2,777, 179, 2,809,473). JP 2004/196716 describes stilbene compounds that have a trisubstituted double bond.

It is a problem to be solved to provide a light-emitting material for an EL device that exhibits good luminous yield with desirable color coordinates, particularly in the blue or blue-green region.

SUMMARY OF THE INVENTION

The invention provides an organic electroluminescent device comprising a cathode, an anode, and having therebetween a light-emitting layer comprising an emissive component represented by formula (I):

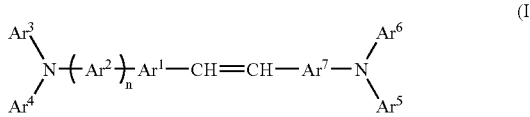

wherein:
$Ar^1$ through $Ar^6$ are independently selected aryl or heteroaryl groups;
$Ar^7$ is a phenyl or fused ring aryl group or a heteroaryl group; and
provided that two aryl or heteroaryl rings may be joined;
n is 1, 2, or 3.

$Ar^1$ through $Ar^6$ are independently selected aryl groups and may each represent phenyl groups, fused aromatic rings such as naphthyl, anthranyl or phenanthryl, heterocyclic aromatic rings wherein one or more carbon atoms have replaced by nitrogen, oxygen or sulfur, and monovalently linked aromatic rings such as biphenyl, and $Ar^1$ through $Ar^6$ may be unsubstituted or further substituted in those ring positions bearing hydrogens. Additionally $Ar^3$ and $Ar^4$ may be joined directly or through additional atoms to form a carbocyclic or heterocyclic ring. $Ar^5$ and $Ar^6$ may be joined directly or through additional atoms to form a carbocyclic or heterocyclic ring. $Ar^7$ is phenyl, a fused ring aromatic carbocyclic group or a heterocyclic group. $Ar^7$ may be unsubstituted or further substituted in those ring positions bearing hydrogens.

The invention also includes a composition based on formula (1) and a lighting device or display incorporating the device and a process for producing light using the device.

The device of the invention provides a light-emitting material for an EL device that exhibits good luminous yield with desirable color coordinates, particularly in the blue or blue-green region.

DETAILED DESCRIPTION OF THE INVENTION

Figure 1:
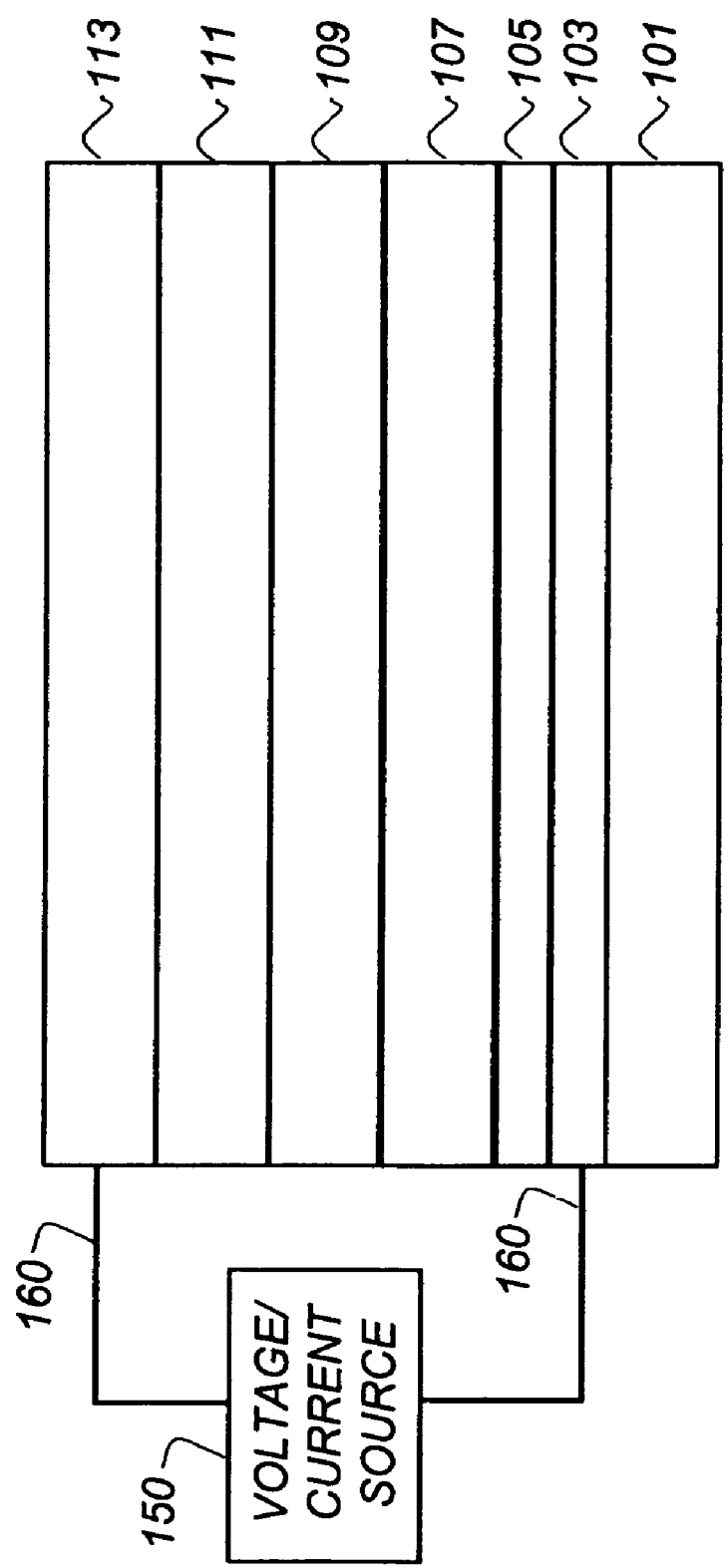
FIG. 1 shows a schematic cross-section of a typical OLED device in which this invention may be used.

The invention is summarized above. An electroluminescent device of the invention may be a multilayer device comprising a cathode, an anode, charge-injecting layers (if necessary), charge-transporting layers, and a light-emitting layer (LEL) comprising a host and at least one light-emitting material. Desirably the light emitting layer comprises a blue or blue-green emitting dopant of Formula (I).

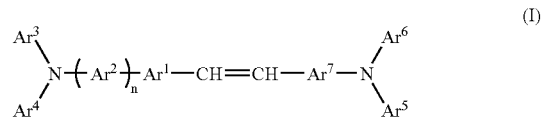

In Formula (Ia), $Ar^1$, each $Ar^2$, and $Ar^3$ through $Ar^6$ represent independently selected aryl groups and may each represent phenyl groups, fused aromatic rings such as naphthyl, anthranyl or phenanthryl, heterocyclic aromatic rings, such as pyridyl wherein one or more carbon atoms have replaced by nitrogen, oxygen or sulfur, and monovalently linked aromatic rings such as biphenyl, and $Ar^1$ through $Ar^6$ may be unsubstituted or further substituted in those ring positions bearing hydrogens. Examples of desirable groups for $Ar^1$ through $Ar^6$ are shown in Table A wherein $R^1$ through $R^3$ represent one or more substituent groups that can be the same or different and individually represent hydrogen or one or more substituents. For example, substituents can be alkyl groups, such as methyl groups, alkoxy groups, such as methoxy, aryl groups, such as phenyl, a halogen such as chlorine, or aryloxygroups, such as phenoxy. Additionally $Ar^3$ and $Ar^4$ may be joined directly or through additional atoms to form a carbocyclic or heterocyclic ring, and $Ar^5$ and $Ar^6$ may be joined directly or through additional atoms to form a carbocyclic or heterocyclic ring. $Ar^7$ is a phenyl group, a fused aromatic group such as naphthyl, anthranyl or phenanthryl, or heterocyclic aromatic rings, such as pyridyl wherein one or more carbon atoms have replaced by nitrogen, oxygen or sulfur.

The double bond shown in formula (I) is only disubstituted. Further substitution of this double bond can lead to a decrease in florescent quantum yield, which is undesirable because it may result in a loss in efficiency when used as a light-emitting material in an OLED device.

In one desirable embodiment, $Ar^1$, each $Ar^2$, and $Ar^3$ through $Ar^7$ are hydrocarbons and thus do not contain a heteroatom. In another suitable aspect of the invention, at least one $Ar^2$ represents a divalent heteroaryl group, such as a nitrogen containing heteroaryl group, which may contain additional fused rings. For example, a pyridinediyl group, a quinolinediyl group, a benzothiazolediyl group, a benzoxazolediyl group, or a thiophenediyl group.

In Formula (I), n is 1, 2, or 3. In one suitable embodiment, n is 1 or 2.

In one desirable embodiment of the invention the emissive blue or blue-green dopant is represented by Formula (II)

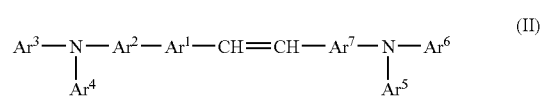

where $Ar^1$ through $Ar^6$ are independently selected aryl groups and may each represent phenyl groups, fused aromatic rings such as naphthyl, anthranyl or phenanthryl, heterocyclic aromatic rings wherein one or more carbon atoms have replaced by nitrogen, oxygen or sulfur, and monovalently linked aromatic rings such as biphenyl, and $Ar^1$ through $Ar^7$ may be unsubstituted or further substituted in those ring positions bearing hydrogens. Additionally $Ar^3$ and $Ar^4$ may be joined directly or through additional atoms to form a carbocyclic or heterocyclic ring, and $Ar^5$ and $Ar^6$ may be joined directly or through additional atoms to form a carbocyclic or heterocyclic ring, $Ar^7$ is phenyl, a fused ring aromatic carbocyclic group or a heterocyclic group. $Ar^7$ may be unsubstituted or further substituted in those ring positions bearing hydrogens.

Examples of desirable groups for $Ar^1$ through $Ar^6$ are shown in Table 1 wherein $R^1$ through $R^3$ represent one or more substituent groups and can be the same or different and individually represent hydrogen, a bond to another atom or one or more substituents. For example, substituents can be alkyl groups, such as methyl or t-butyl groups, alkoxy groups, such as methoxy, aryl groups, such as phenyl, a halogen such as chlorine, or aryloxygroups, such as phenoxy. Additionally $Ar^3$ and $Ar^4$ may be joined directly or through additional atoms to form a carbocyclic or heterocyclic ring, and $Ar^5$ and $Ar^6$ may be joined directly or through additional atoms to form a carbocyclic or heterocyclic ring. Examples of desirable groups for $Ar^7$ are shown in Table B wherein $R^1$ through $R^3$ represent one or more substituent groups and can be the same or different and individually represent hydrogen or one or more substituents. For example, substituents can be alkyl groups, such as methyl groups, alkoxy groups, such as methoxy, aryl groups, such as phenyl, a halogen such as chlorine, or aryloxygroups, such as phenoxy.

TABLE A

Examples of Independently Selected Aryl Groups in Formula (I) and Formula (II)

TABLE A-continued

Examples of Independently Selected Aryl Groups in Formula (I) and Formula (II)

wherein R¹ through R³ represent one or more substituent groups and individually represent hydrogen or one or more substituents, including but not limited to alkyl groups, such as methyl groups, alkoxy groups, such as methoxy, aryl groups, such as phenyl, a halogen such as chlorine, or aryloxygroups, such as phenoxy.

TABLE B

Examples of Independently Selected Aryl Groups for $Ar^7$
in Formula (I) and Formula (II)

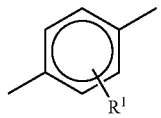

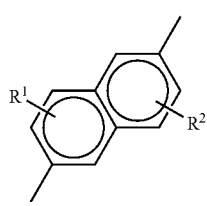

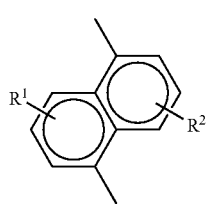

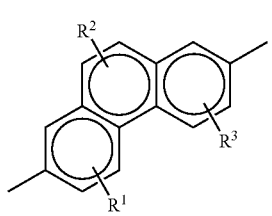

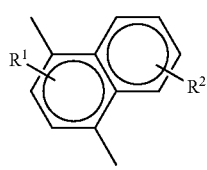

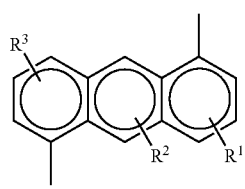

TABLE B-continued

Examples of Independently Selected Aryl Groups for $Ar^7$
in Formula (I) and Formula (II)

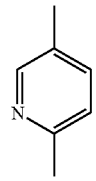

wherein R¹ through R³ represent one or more substituent groups and individually represent hydrogen or one or more substituents, including but not limited to alkyl groups, such as methyl groups, alkoxy groups, such as methoxy, amine groups such as dimethylamino or diphenylamino, cyano groups, aryl groups, such as phenyl, a halogen such as fluorine, heterocyclic groups such as benzothiazole or aryloxygroups, such as phenoxy.

In one embodiment, Ar and R groups are selected to provide a compound with a sublimation temperature less than 204° C.

In a particularly desirable embodiment of the invention, the light emitting layer comprises a blue or blue-green dopant of Formula (III)

(III)

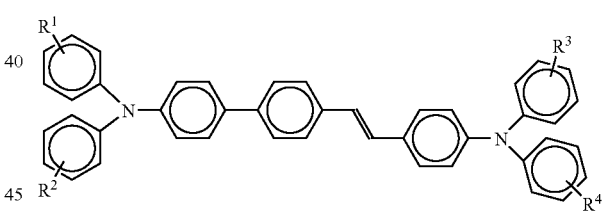

wherein R¹ through R³ represent one or more substituent groups and individually represent hydrogen or one or more substituents, for example, alkyl groups, such as methyl groups or tert-butyl groups, alkoxy groups, such as methoxy, amino groups such as diphenylamino, ditolylamino and dimethylamino, aryl groups, such as substituted or unsubstituted phenyl, halogen groups such as fluoro, fluorinated groups such as trifluoromethyl, cyano groups, heterocyclic groups such as benzothiazole or aryloxy groups, such as phenoxy.

Blue or blue-green color, as used herein, means that the dopant in the device emits a 1931 CIE x coordinate between 0.005 and 0.21 and a 1931 CIE y coordinate between 0.005 and 0.36 when it constitutes the only emitting material.

Particularly useful embodiments of the emissive dopants of this invention are shown in compounds (I-1) through (I-27).

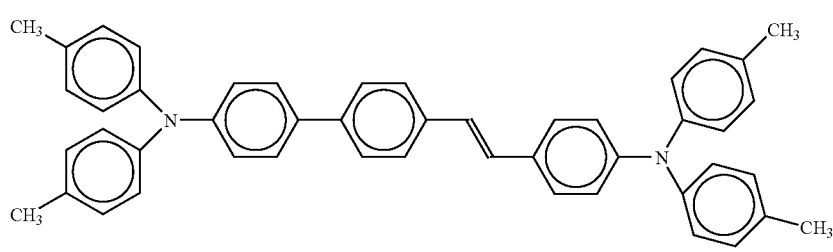
(I-1)
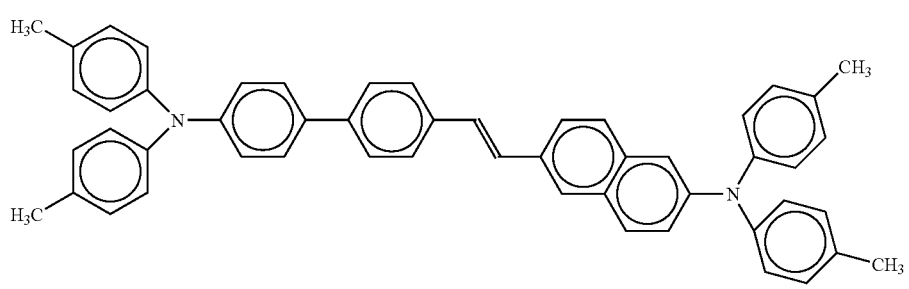
(I-2)
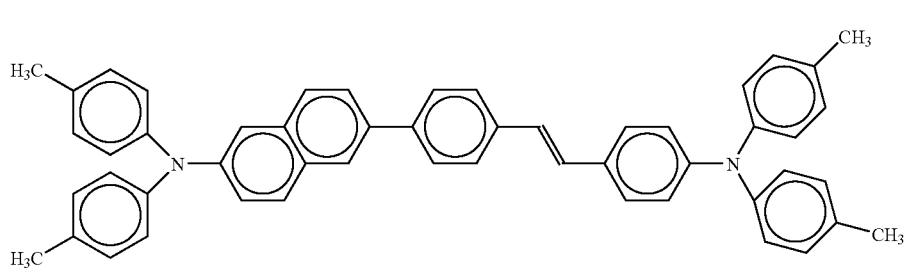
(I-3)
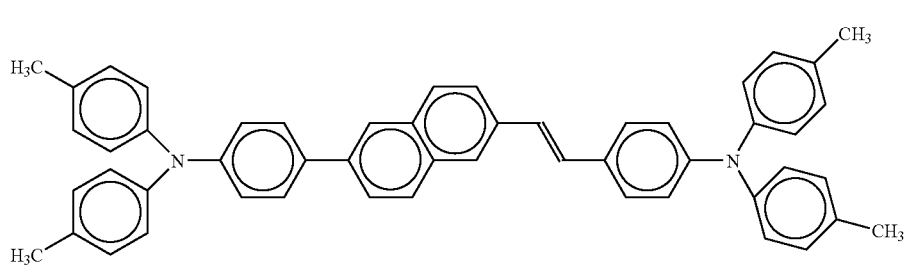
(I-4)
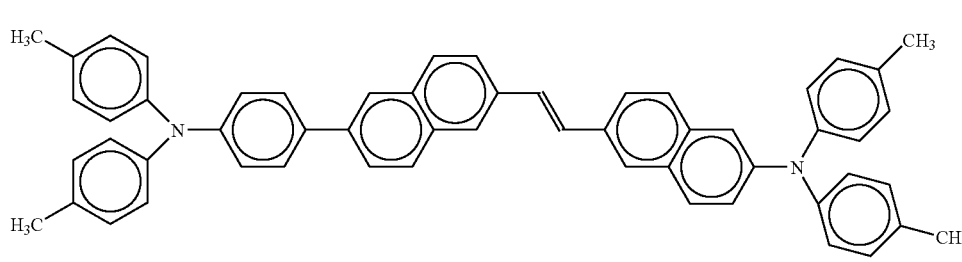
(I-5)
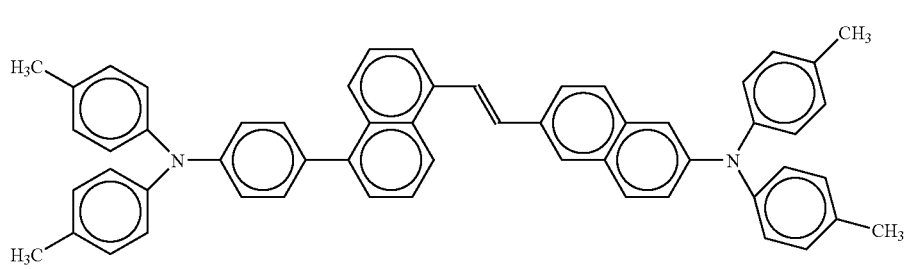
(I-6)

-continued
(I-7)
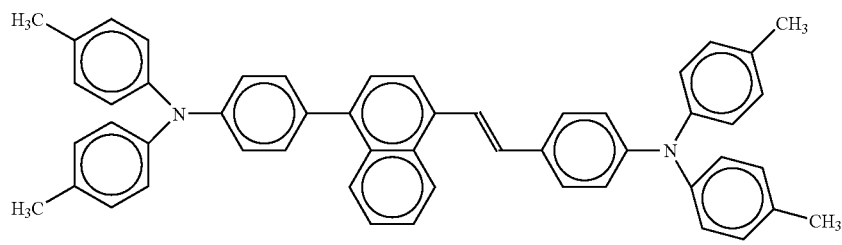
(I-8)
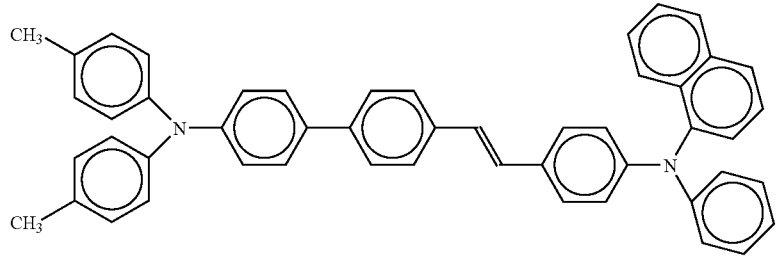
(I-9)
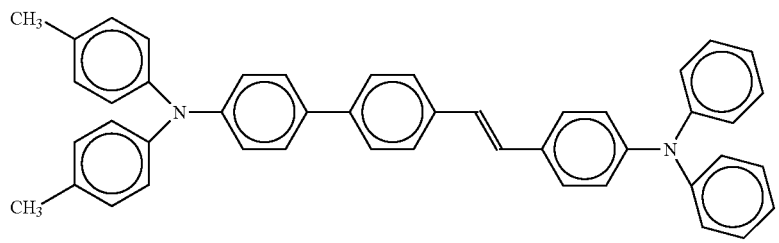
(I-10)
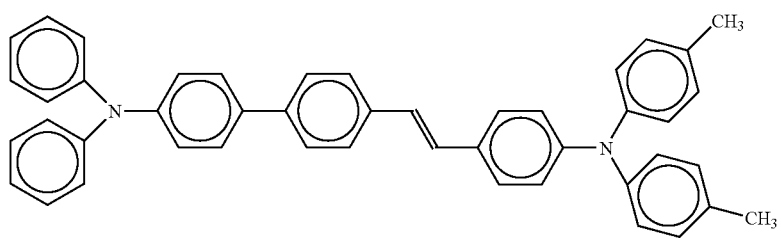
(I-11)
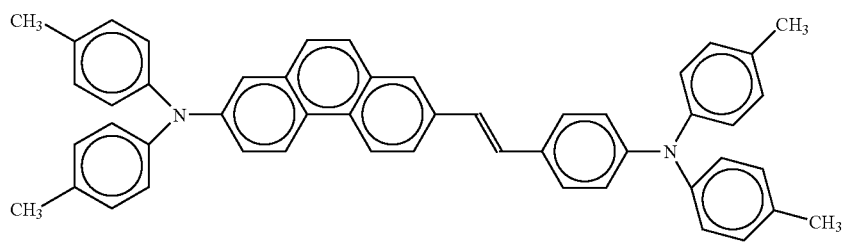
(I-12)
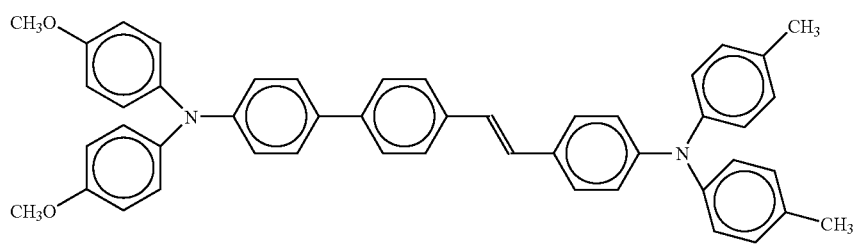

-continued
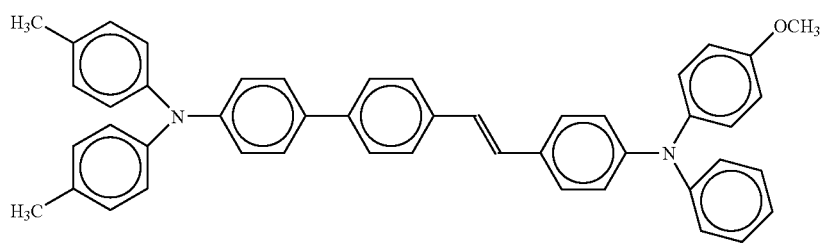
(I-13)
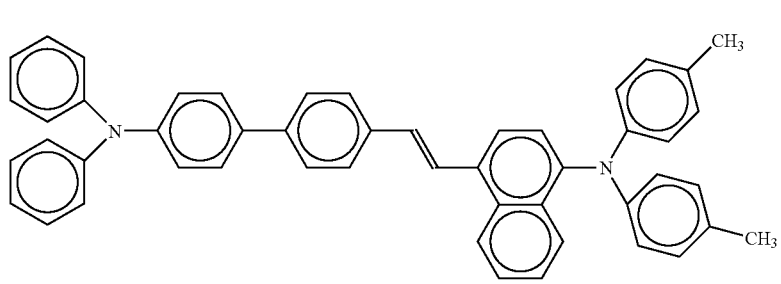
(I-14)
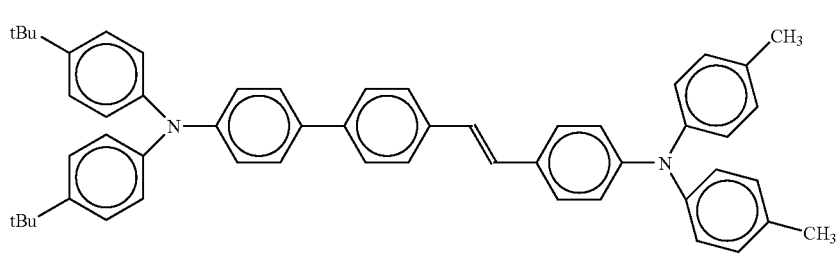
(I-15)
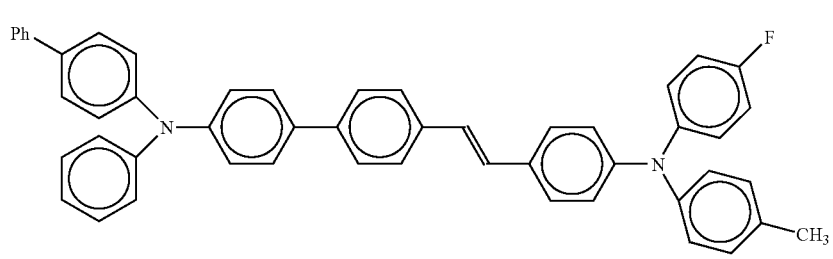
(I-16)
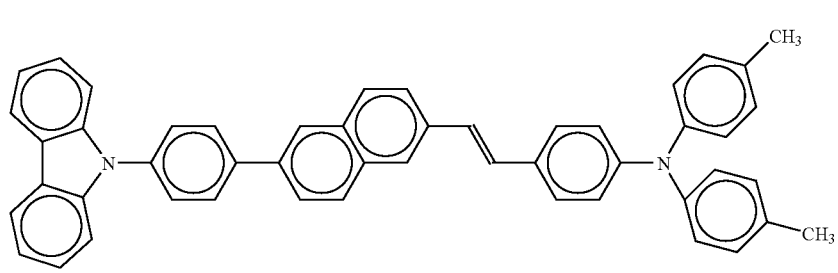
(I-17)
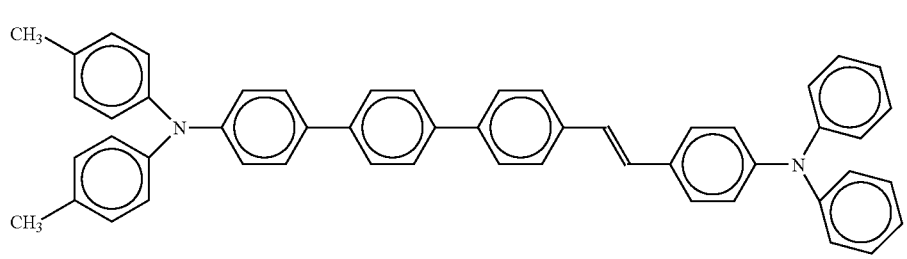
(I-18)

-continued
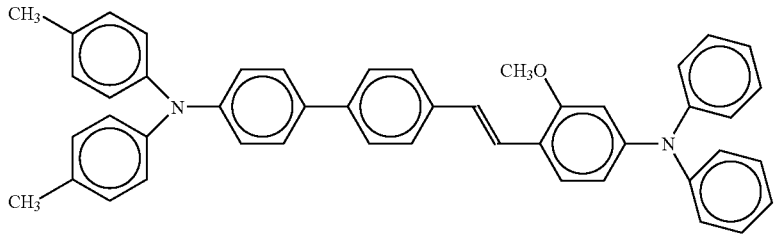
(I-19)
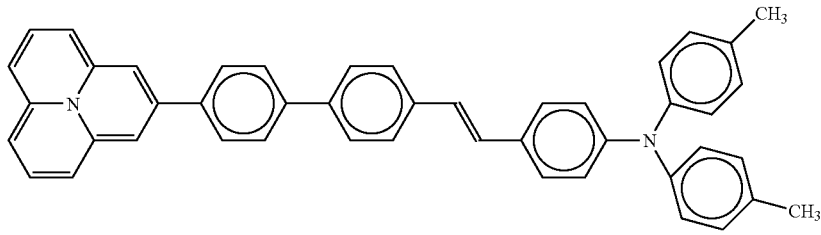
(I-20)
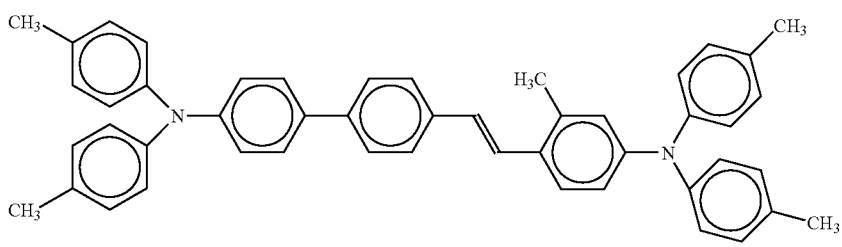
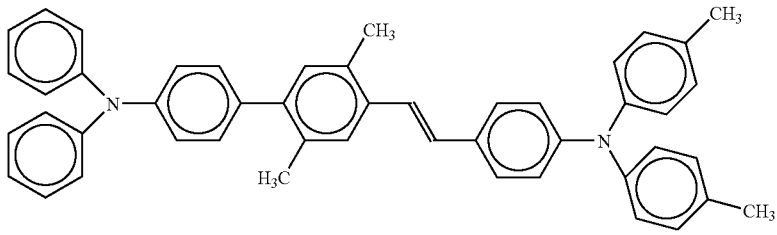
(I-22)
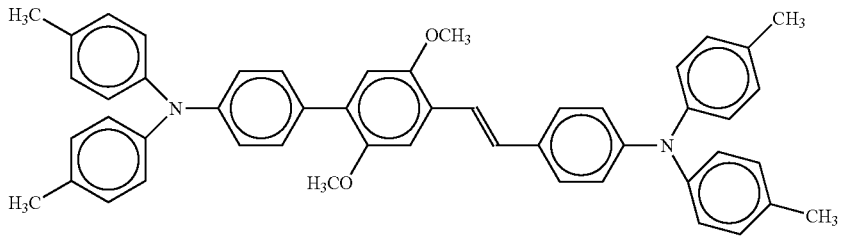
(I-23)
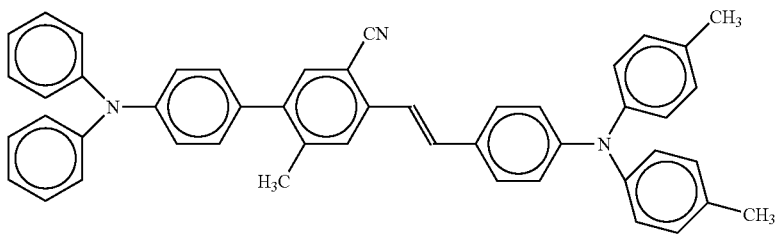
(I-24)

-continued
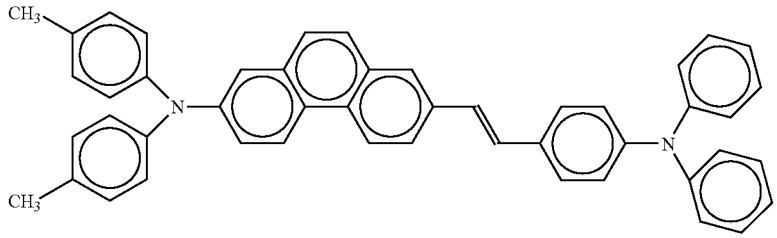
(I-25)
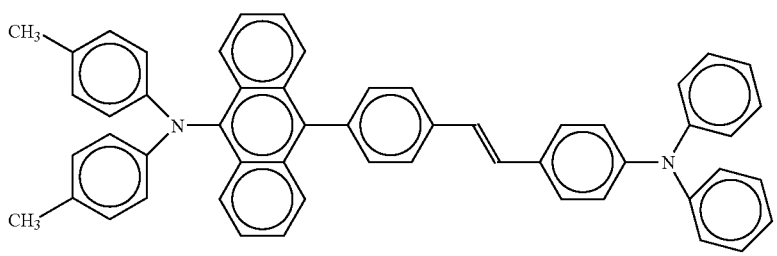
(I-26)
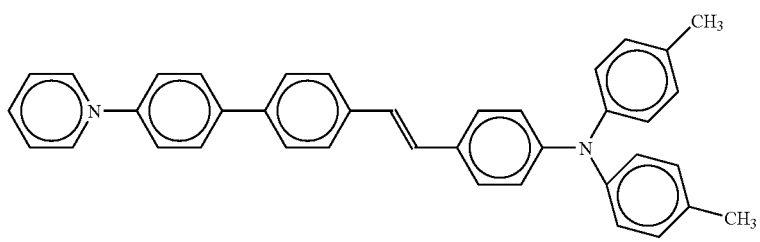
(I-27)
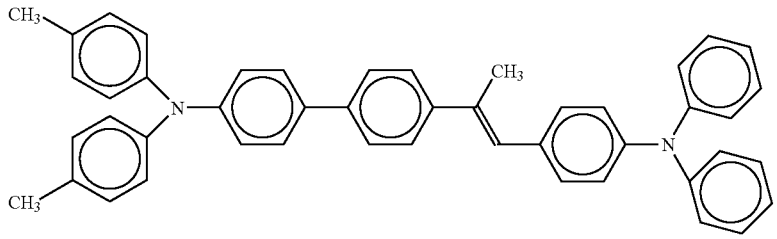
(I-28)
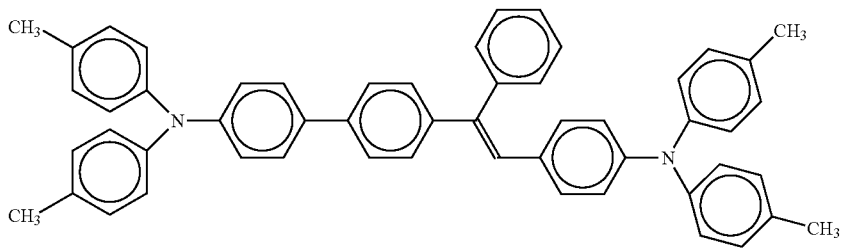
(I-29)

-continued
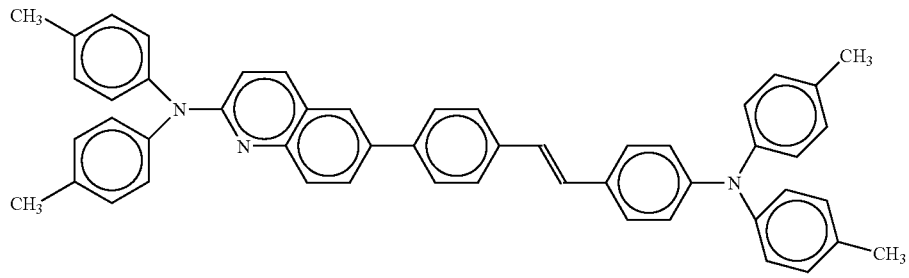
(I-30)
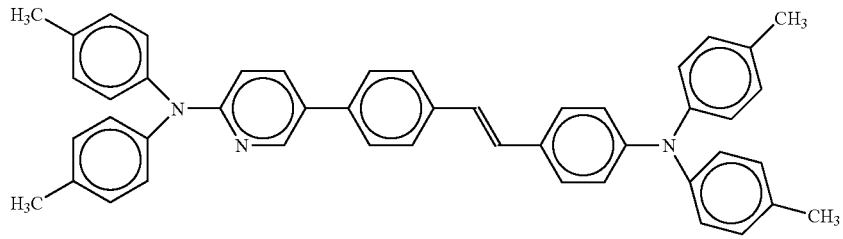
(I-31)
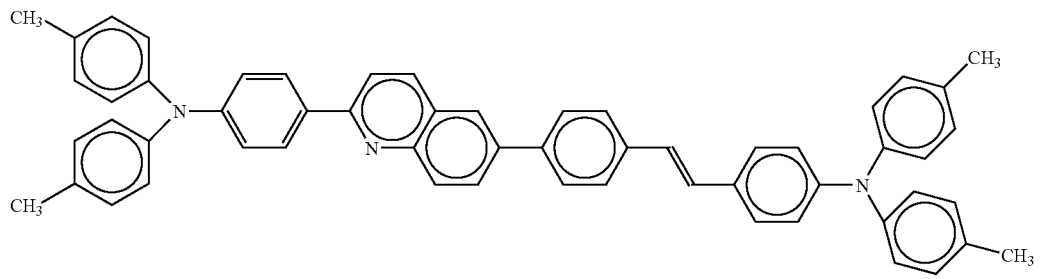
(I-32)
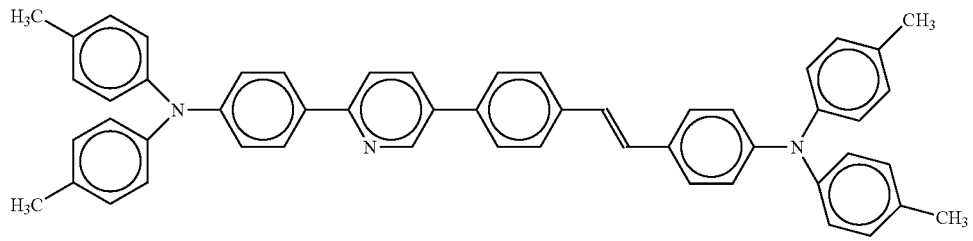
(I-33)
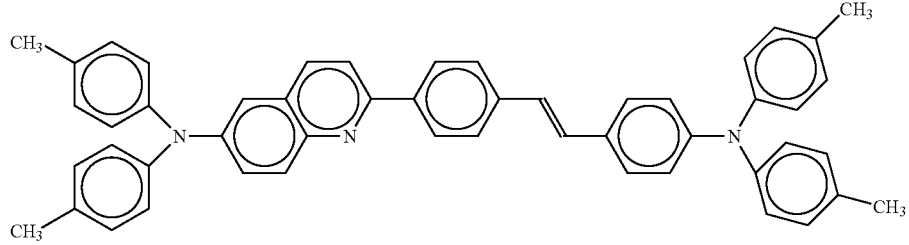
(I-34)
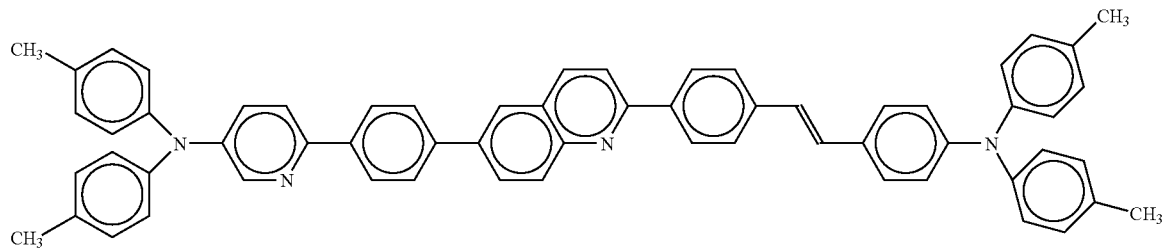
(I-35)

-continued
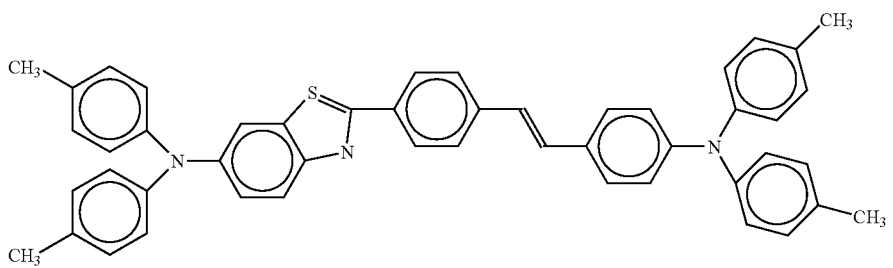
(I-36)
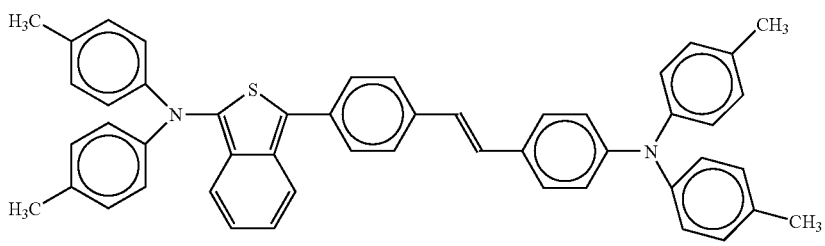
(I-37)
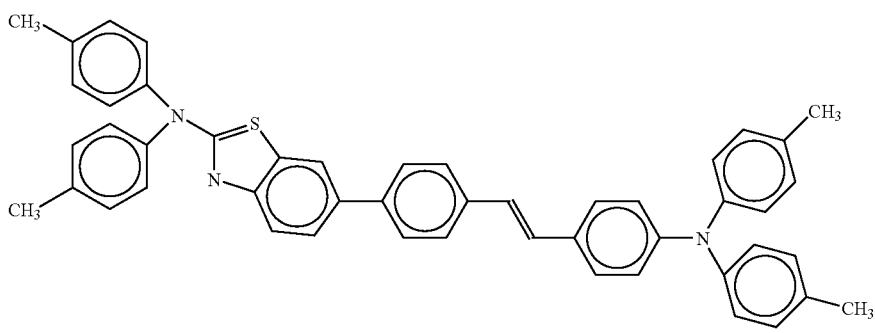
(I-38)
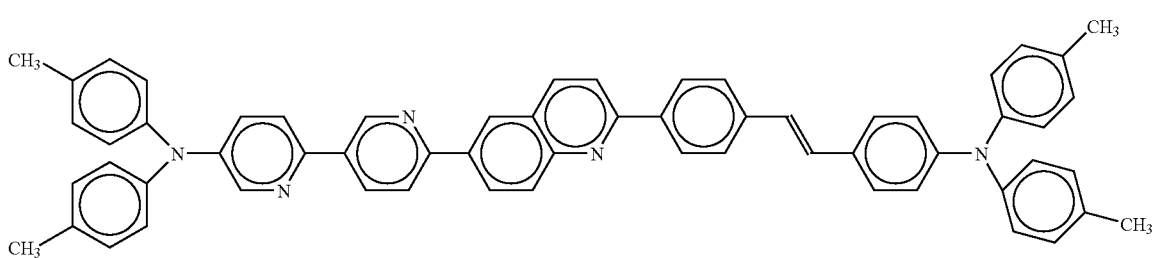
(I-39)
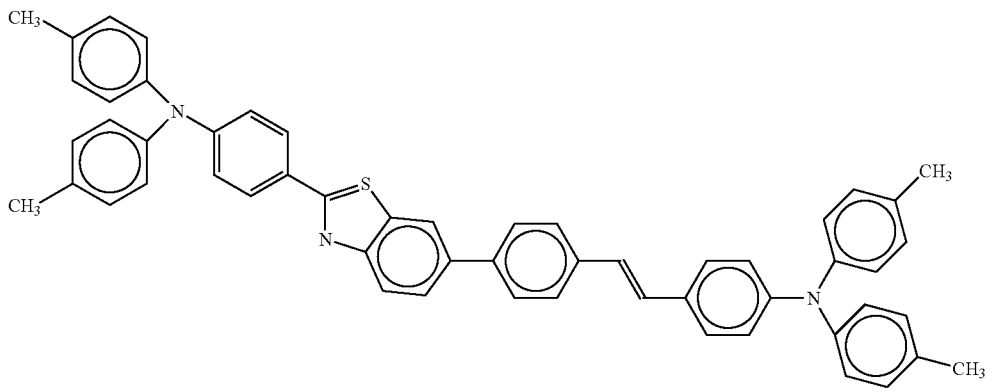
(I-40)

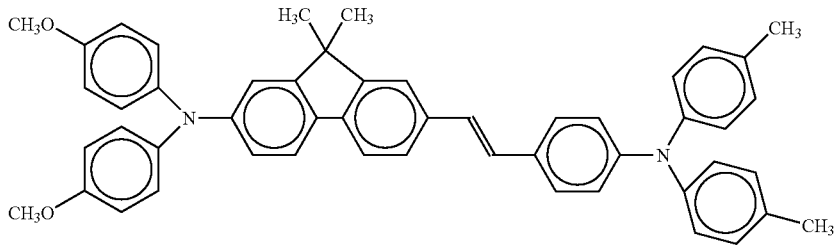

(I-41)

Suitably, the light-emitting layer of the device comprises a host and one or more light-emitting materials where the light-emitting material(s) is present in an amount of up to 10 wt % of the host, more typically from 0.1-10.0 wt %, and desirably 2-6 wt %. At least one light-emitting material is suitably a dopant represented by Formula (1) or Formula (2).

Desirable hosts include those based on a chelated oxinoid compound or an anthracene compound. In one desirable embodiment the host is represented by Formula (IV).

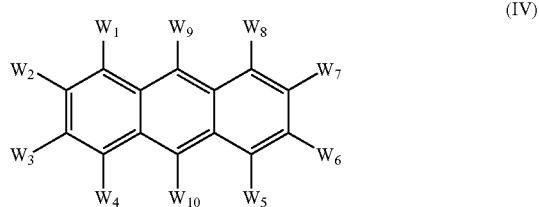

(IV)

In Formula (IV), $W_1$-$W_{10}$ independently represent hydrogen or an independently selected substituent, provided that two adjacent substituents can combine to form rings. In one suitable embodiment, $W^9$ and $W^{10}$ independently represent naphthyl groups. In another desirable embodiment, $W^9$ and $W^{10}$ represent a naphthyl group and a biphenyl group.

Suitable host materials also include anthracene structures described in WO 2004/018587 (asymmetric anthracenes), JP2004059535—(asymmetric anthracenes) and WO2003/087023.

Particular examples of hosts are tris(8-quinolinolato)aluminum (III), 9,10-di-(2-naphthyl)anthracene, 2-tert-butyl-9,10-di-(2-naphthyl)anthracene, 9-(4-biphenyl)-10-(2-naphthyl)anthracene and 9-(4-biphenyl)-10-(1-naphthyl)anthracene. Preferably, the host is selected such that the host absorbs light at a shorter wavelength than the dopant and the emission spectrum of the host overlaps with the absorption spectrum of the dopant.

Embodiments of the dopants useful in the invention can provide a wide range of hues. Embodiments of the dopants especially useful in the invention provide an emitted light having a blue hue or a blue-green hue. In another preferred embodiment, dopants useful in the invention are used in an electroluminescent device that emits white light.

Embodiments of the invention provide not only improved luminous yield but also a desirable blue or blue-green hue as evidenced by CIE color coordinates and spectral curve shape and location Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecyl-benzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron, such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

General Device Architecture

The present invention can be employed in many EL device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light-emitting layer located between the anode and cathode. Additional layers may be employed as more fully described hereafter.

A typical structure according to the present invention and especially useful for a small molecule device, is shown in FIG. 1 and is comprised of a substrate 101, an anode 103, a hole-injecting layer 105, a hole-transporting layer 107, a light-emitting layer 109, an electron-transporting layer 111, and a cathode 113. These layers are described in detail below. Note that the substrate 101 may alternatively be located adjacent to the cathode 113, or the substrate 101 may actually constitute the anode 103 or cathode 113. The organic layers between the anode 103 and cathode 113 are conveniently referred to as the organic EL element. Also, the total combined thickness of the organic layers is desirably less than 500 nm. If the device includes phosphorescent material, a hole-blocking layer, located between the light-emitting layer and the electron-transporting layer, may be present.

The anode 103 and cathode 113 of the OLED are connected to a voltage/current source 150 through electrical conductors 160. The OLED is operated by applying a potential between the anode 103 and cathode 113 such that the anode 103 is at a more positive potential than the cathode 113. Holes are injected into the organic EL element from the anode 103 and electrons are injected into the organic EL element at the cathode 113. Enhanced device stability can sometimes be achieved when the OLED is operated in an AC mode where, for some time period in the AC cycle, the potential bias is reversed and no current flows. An example of an AC driven OLED is described in U.S. Pat. No. 5,552,678.

Substrate

The OLED device of this invention is typically provided over a supporting substrate 101 where either the cathode 113 or anode 103 can be in contact with the substrate. The electrode in contact with the substrate 101 is conveniently referred to as the bottom electrode. Conventionally, the bottom electrode is the anode 103, but this invention is not limited to that configuration. The substrate 101 can either be light transmissive or opaque, depending on the intended direction of light emission. The light transmissive property is desirable for viewing the EL emission through the substrate 101. Transparent glass or plastic is commonly employed in such cases. The substrate 101 can be a complex structure comprising multiple layers of materials. This is typically the case for active matrix substrates wherein TFTs are provided below the OLED layers. It is still necessary that the substrate 101, at least in the emissive pixelated areas, be comprised of largely transparent materials such as glass or polymers. For applications where the EL emission is viewed through the top electrode, the transmissive characteristic of the bottom support is immaterial, and therefore the substrate can be light transmissive, light absorbing or light reflective. Substrates for use in this case include, but are not limited to, glass, plastic, semiconductor materials such as silicon, ceramics, and circuit board materials. Again, the substrate 101 can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode 103 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 103. For applications where EL emission is viewed only through the cathode 113, the transmissive characteristics of the anode 103 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize short circuits or enhance reflectivity.

Cathode

When light emission is viewed solely through the anode 103, the cathode 113 used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)), the cathode being capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode 113 must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP 1 076 368, U.S. Pat. Nos. 6,278,236, and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Hole-Injecting Layer (HIL)

A hole-injecting layer 105 may be provided between anode 103 and hole-transporting layer 107. The hole-injecting layer can serve to improve the film formation property of subsequent organic layers and to facilitate injection of holes into the hole-transporting layer 107. Suitable materials for use in the hole-injecting layer 105 include, but are not limited to, porphyrinic compounds as described in U.S. Pat. No. 4,720,432, plasma-deposited fluorocarbon polymers as described in U.S. Pat. No. 6,208,075, and some aromatic amines, for example, MTDATA (4,4',4"-tris[(3-methylphenyl)phenylamino]triphenylamine). Alternative hole-injecting materials reportedly useful in organic EL devices are described in EP 0 891 121 A1 and EP 1 029 909 A1. A hole-injection layer is conveniently used in the present invention, and is desirably a plasma-deposited fluorocarbon polymer. The thickness of a hole-injection layer containing a plasma-deposited fluorocarbon polymer can be in the range of 0.2 nm to 15 nm and suitably in the range of 0.3 to 1.5 nm.

Hole-Transporting Layer (HTL)

While not always necessary, it is often useful to include a hole-transporting layer in an OLED device. The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines is those which include at least two aromatic tertiary amine moieties as described in U.S. Pat. Nos. 4,720,432 and 5,061,569. Such compounds include those represented by structural formula (A).

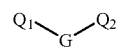

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

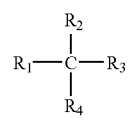

B where $R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural formula (C):

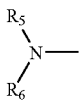

C wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines is the tetraaryldiamines. Desirable tetraaryldiamines include two diarylamino groups, such as indicated by formula (C), linked through an arylene group. Useful tetraaryldiamines include those represented by formula (D).

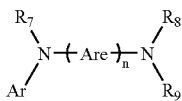

D wherein
each Are is an independently selected arylene group, such as a phenylene or anthracene moiety,
n is an integer of from 1 to 4, and
Ar, $R_7$, $R_8$, and $R_9$ are independently selected aryl groups.
In a typical embodiment, at least one of Ar, $R_7$, $R_8$, and $R_9$ is a polycyclic fused ring structure, e.g., a naphthalene.

The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halide such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are usually phenyl and phenylene moieties.

The hole-transporting layer can be formed of a single tertiary amine compound or a mixture of such compounds. Specifically, one may employ a triarylamine, such as a triarylamine satisfying the formula (B), in combination with a tetraaryldiamine, such as indicated by formula (D). Illustrative of useful aromatic tertiary amines are the following:

1,1-Bis(4-di-p-tolylaminophenyl)cyclohexane (TAPC)
1,1-Bis(4-di-p-tolylaminophenyl)-4-methylcyclohexane
1,1-Bis(4-di-p-tolylaminophenyl)-4-phenylcyclohexane
1,1-Bis(4-di-p-tolylaminophenyl)-3-phenylpropane (TAPPP)
N,N,N',N'-tetraphenyl-4,4'''-diamino-1,1':4',1'':4'',1'''-quaterphenyl Bis(4-dimethylamino-2-methylphenyl)phenylmethane
1,4-bis[2-[4-[N,N-di(p-toly)amino]phenyl]vinyl]benzene (BDTAPVB)
N,N,N',N'-Tetra-p-tolyl-4,4'-diaminobiphenyl (TTB)
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl (NPB)
4,4'-Bis[N-(1-naphthyl)-N-(2-naphthyl)amino]biphenyl (TNB)
4,4'-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4'-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4''-diamino-p-terphenyl
4,4'-Bis {N-phenyl-N-[4-(1-naphthyl)-phenyl]amino}biphenyl
2,6-Bis[N,N-di(2-naphthyl)amino]fluorene
4,4',4''-tris[(3-methylphenyl)phenylamino]triphenylamine (MTDATA)
4,4'-Bis[N-(3-methylphenyl)-N-phenylamino]biphenyl (TPD)

Another class of useful hole-transporting materials includes polycyclic aromatic compounds as described in EP 1 009 041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS. It is also possible for the hole-transporting layer to comprise two or more sublayers of differing compositions, the composition of each sublayer being as described above. The thickness of the hole-transporting layer can be between 10 and about 500 nm and suitably between 50 and 300 nm.

Light-Emitting Layer (LEL)

In addition to the light-emitting materials of this invention, additional light emitting materials may be used in the EL device, including other fluorescent materials. Other fluorescent materials may be used in the same layer as the blue or blue-green dopant material, in adjacent layers, in adjacent pixels, or any combination.

As more fully described in U.S. Pat. Nos. 4,769,292 and 5,935,721, the light-emitting layer (LEL) of the organic EL element includes a luminescent material where electroluminescence is produced as a result of electron-hole pair recombination. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material.

The host and emitting materials can be small non-polymeric molecules or polymeric materials such as polyfluorenes and polyvinylarylenes (e.g., poly(p-phenylenevinylene), PPV). In the case of polymers, small-molecule emitting materials can be molecularly dispersed into a polymeric host, or the emitting materials can be added by copolymerizing a minor constituent into a host polymer. Host materials may be mixed together in order to improve film formation, electrical properties, light emission efficiency, operating lifetime, or manufacturability. The host may comprise a material that has good hole-transporting properties and a material that has good electron-transporting properties.

An important relationship for choosing a fluorescent material as a guest emitting material is a comparison of the excited singlet-state energies of the host and the fluorescent material. It is highly desirable that the excited singlet-state energy of the fluorescent material be lower than that of the host material. The excited singlet-state energy is defined as the difference in energy between the emitting singlet state and the ground state. For non-emissive hosts, the lowest excited state of the same electronic spin as the ground state is considered the emitting state.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, 6,020,078.

Metal complexes of 8-hydroxyquinoline and similar derivatives, also known as metal-chelated oxinoid compounds (Formula E), constitute one class of useful host compounds capable of supporting electroluminescence, and are particularly suitable for light emission of wavelengths longer than 500 nm, e.g., green, yellow, orange, and red.

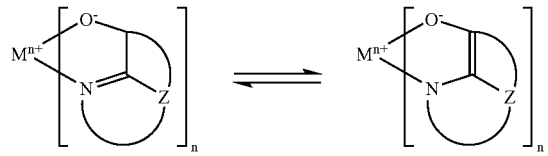

E wherein
M represents a metal;
n is an integer of from 1 to 4; and
Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; a trivalent metal, such aluminum or gallium, or another metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]

CO-2: Magnesium bisoxine [alias, bis(8-quinolinolato) magnesium(II)]

CO-3: Bis[benzo {f}-8-quinolinolato]zinc (II)

CO-4: Bis(2-methyl-8-quinolinolato)aluminum(III)-□-oxo-bis(2-methyl-8-quinolinolato) aluminum(III)

CO-5: Indium trisoxine [alias, tris(8-quinolinolato)indium]

CO-6: Aluminum tris(5-methyloxine) [alias, tris(5-methyl-8-quinolinolato) aluminum(III)]

CO-7: Lithium oxine [alias, (8-quinolinolato)lithium(I)]

CO-8: Gallium oxine [alias, tris(8-quinolinolato)gallium (III)]

CO-9: Zirconium oxine [alias, tetra(8-quinolinolato)zirconium(IV)]

Derivatives of 9,10-di-(2-naphthyl)anthracene (Formula F) constitute one class of useful host materials capable of supporting electroluminescence, and are particularly suitable for light emission of wavelengths longer than 400 nm, e.g., blue, green, yellow, orange or red.

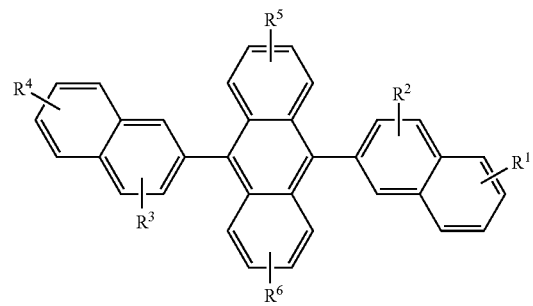

F wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;

Group 2: aryl or substituted aryl of from 5 to 20 carbon atoms;

Group 3: carbon atoms from 4 to 24 necessary to complete a fused aromatic ring of anthracenyl; pyrenyl, or perylenyl;

Group 4: heteroaryl or substituted heteroaryl of from 5 to 24 carbon atoms as necessary to complete a fused heteroaromatic ring of furyl, thienyl, pyridyl, quinolinyl or other heterocyclic systems;

Group 5: alkoxylamino, alkylamino, or arylamino of from 1 to 24 carbon atoms; and Group 6: fluorine, chlorine, bromine or cyano.

Illustrative examples include 9,10-di-(2-naphthyl)anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene.

The monoanthracene derivative of Formula (I) is also a useful host material capable of supporting electroluminescence, and are particularly suitable for light emission of wavelengths longer than 400 nm, e.g., blue, green, yellow, orange or red. Anthracene derivatives of Formula (I) is described in commonly assigned U.S. patent application Ser. No. 10/693,121 filed Oct. 24, 2003 by Lelia Cosimbescu et al., entitled "Electroluminescent Device With Anthracene Derivative Host", the disclosure of which is herein incorporated by reference,

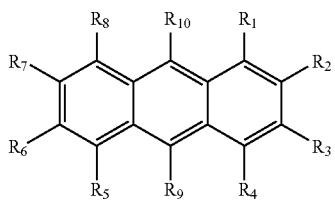

(IV)

wherein:

R$_1$-R$_8$ are H; and

R$_9$ is a naphthyl group containing no fused rings with aliphatic carbon ring members; provided that R$_9$ and R$_{10}$ are not the same, and are free of amines and sulfur compounds. Suitably, R$_9$ is a substituted naphthyl group with one or more further fused rings such that it forms a fused aromatic ring system, including a phenanthryl, pyrenyl, fluoranthene, perylene, or substituted with one or more substituents including fluorine, cyano group, hydroxy, alkyl, alkoxy, aryloxy, aryl, a heterocyclic oxy group, carboxy, trimethylsilyl group, or an unsubstituted naphthyl group of two fused rings. Conveniently, R$_9$ is 2-naphthyl, or 1-naphthyl substituted or unsubstituted in the para position; and R$_{10}$ is a biphenyl group having no fused rings with aliphatic carbon ring members. Suitably R$_{10}$ is a substituted biphenyl group, such that is forms a fused aromatic ring system including but not limited to a naphthyl, phenanthryl, perylene, or substituted with one or more substituents including fluorine, cyano group, hydroxy, alkyl, alkoxy, aryloxy, aryl, a heterocyclic oxy group, carboxy, trimethylsilyl group, or an unsubstituted biphenyl group. Conveniently, R$_{10}$ is 4-biphenyl, 3-biphenyl unsubstituted or substituted with another phenyl ring without fused rings to form a terphenyl ring system, or 2-biphenyl. Particularly useful is 9-(2-naphthyl)-10-(4-biphenyl)anthracene.

Another useful class of anthracene derivatives is represented by general formula (V)

$$A1\text{--}L\text{--}A2 \quad (V)$$

wherein A 1 and A 2 each represent a substituted or unsubstituted monophenyl-anthryl group or a substituted or unsubstituted diphenylanthryl group and can be the same with or different from each other and L represents a single bond or a divalent linking group.

Another useful class of anthracene derivatives is represented by general formula (VI)

$$A3\text{--}An\text{--}A4 \quad (VI)$$

wherein An represents a substituted or unsubstituted divalent anthracene residue group, A 3 and A 4 each represent a substituted or unsubstituted monovalent condensed aromatic ring group or a substituted or unsubstituted non-condensed ring aryl group having 6 or more carbon atoms and can be the same with or different from each other.

Asymmetric anthracene derivatives as disclosed in U.S. Pat. No. 6,465,115 and WO 2004/018587 are useful hosts and these compounds are represented by general formulas (VII) and (VIII) shown below, alone or as a component in a mixture

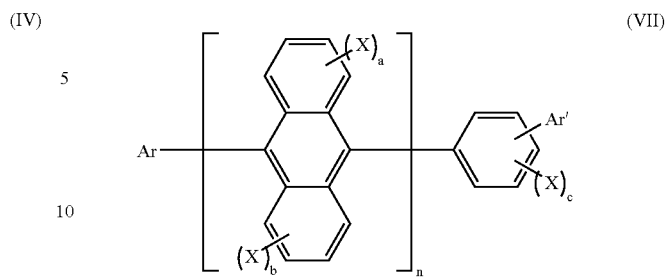

(VII)

wherein:

Ar is an (un)substituted condensed aromatic group of 10-50 nuclear carbon atoms;

Ar' is an (un)substituted aromatic group of 6-50 nuclear carbon atoms;

X is an (un)substituted aromatic group of 6-50 nuclear carbon atoms, (un)substituted aromatic heterocyclic group of 5-50 nuclear carbon atoms, (un)substituted alkyl group of 1-50 carbon atoms, (un)substituted alkoxy group of 1-50 carbon atoms, (un)substituted aralkyl group of 6-50 carbon atoms, (un)substituted aryloxy group of 5-50 nuclear carbon atoms, (un)substituted arylthio group of 5-50 nuclear carbon atoms, (un)substituted alkoxycarbonyl group of 1-50 carbon atoms, carboxy group, halogen atom, cyano group, nitro group, or hydroxy group;

a, b, and c are whole numbers of 0-4; and n is a whole number of 1-3;

and when n is 2 or more, the formula inside the parenthesis shown below can be the same or different.

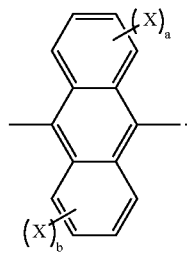

Furthermore, the present invention provides anthracene derivatives represented by general formula (VIII) shown below

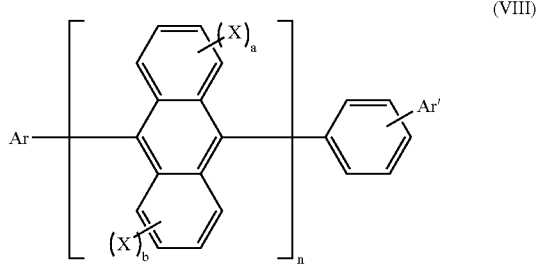

(VIII)

wherein:
Ar is an (un)substituted condensed aromatic group of 10-50 nuclear carbon atoms;

Ar' is an (un)substituted aromatic group of 6-50 nuclear carbon atoms;

X is an (un)substituted aromatic group of 6-50 nuclear carbon atoms, (un)substituted aromatic heterocyclic group of 5-50 nuclear carbon atoms, (un)substituted alkyl group of 1-50 carbon atoms, (un)substituted alkoxy group of 1-50 carbon atoms, (un)substituted aralkyl group of 6-50 carbon atoms, (un)substituted aryloxy group of 5-50 nuclear carbon atoms, (un)substituted arylthio group of 5-50 nuclear carbon atoms, (un)substituted alkoxycarbonyl group of 1-50 carbon atoms, carboxy group, halogen atom, cyano group, nitro group, or hydroxy group;

a, b, and c are whole numbers of 0-4; and n is a whole number of 1-3; and when n is 2 or more, the formula inside the parenthesis shown below can be the same or different

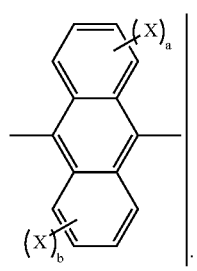

Specific examples of useful anthracene materials for use in a light-emitting layer include

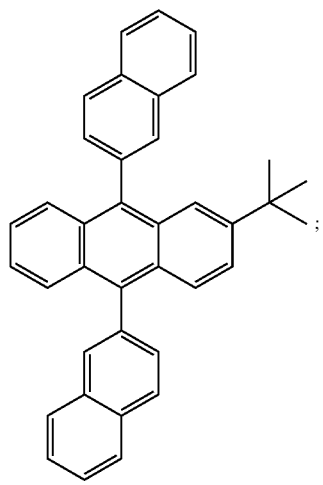

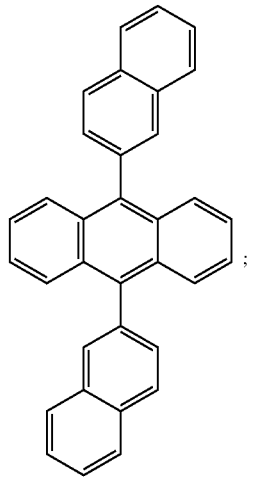

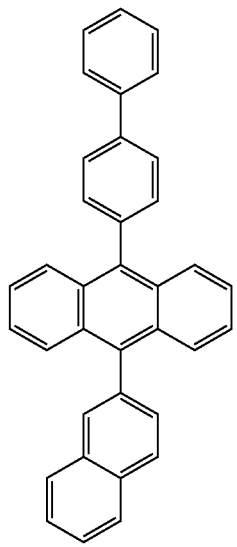

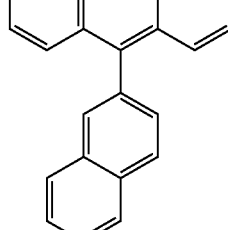

BNA;

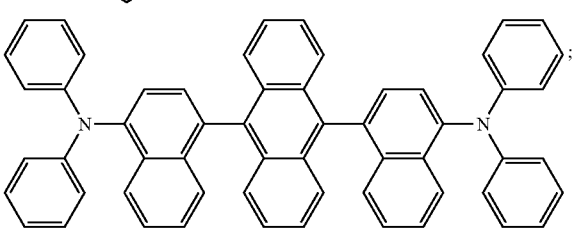

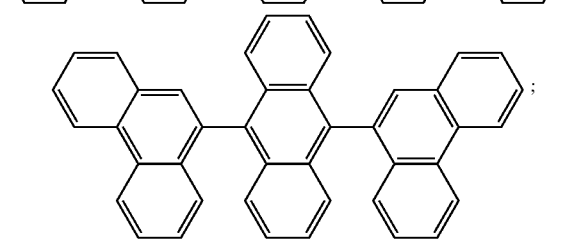

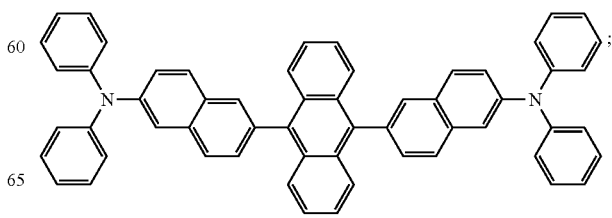

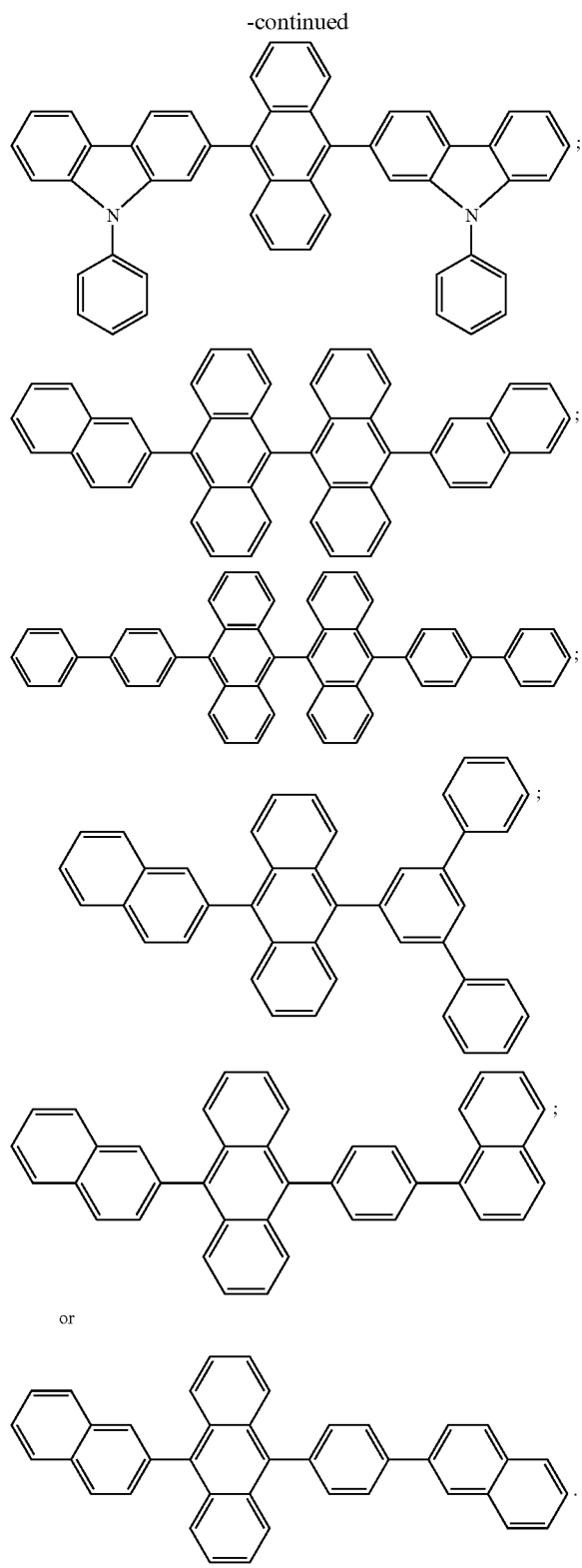

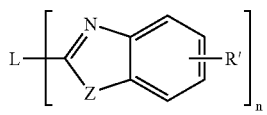

wherein:
n is an integer of 3 to 8;
Z is O, NR or S; and
R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and
L is a linkage unit consisting of alkyl, aryl, substituted alkyl, or substituted aryl, which connects the multiple benzazoles together. L may be either conjugated with the multiple benzazoles or not in conjugation with them. An example of a useful benzazole is 2,2',2"-(1,3,5-phenylene)tris[1-phenyl-1H-benzimidazole].

Styrylarylene derivatives as described in U.S. Pat. No. 5,121,029 and JP 08333569 are also useful hosts for blue emission. For example, 9,10-bis[4-(2,2-diphenylethenyl)phenyl]anthracene and 4,4'-bis(2,2-diphenylethenyl)-1,1'-biphenyl (DPVBi) are useful hosts for blue emission.

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrylium and thiapyrylium compounds, fluorene derivatives, periflanthene derivatives, indenoperylene derivatives, bis(azinyl)imine boron compounds, bis(azinyl)methene compounds, and carbostyryl compounds. Illustrative examples of useful materials include, but are not limited to, the following:

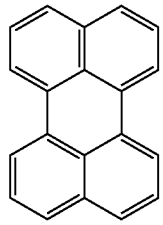

L1

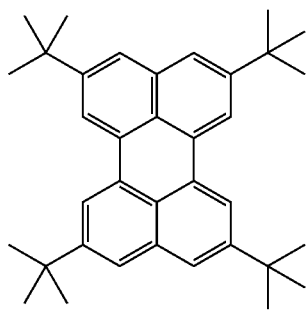

Benzazole derivatives (Formula G) constitute another class of useful host materials capable of supporting electroluminescence, and are particularly suitable for light emission of wavelengths longer than 400 nm, e.g., blue, green, yellow, orange or red.

-continued
L2
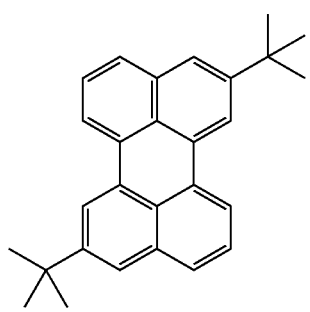
L3
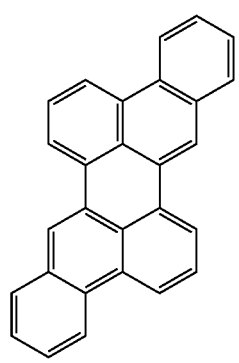
L4
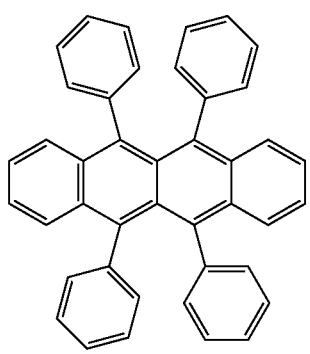
L5
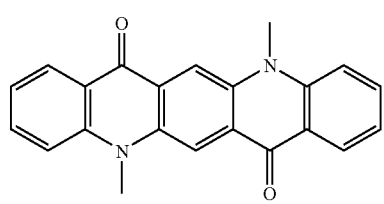
L6
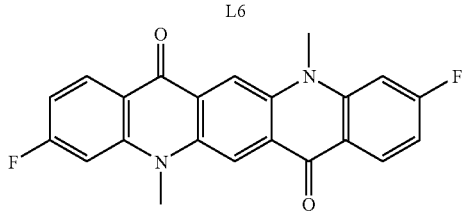
-continued
L7
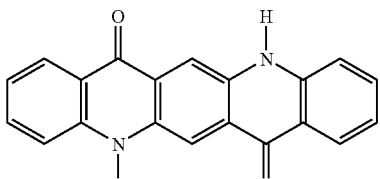
L8
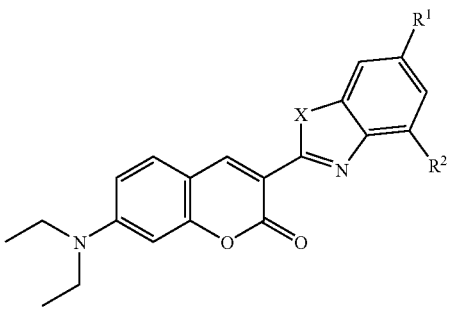
|  | X | R1 | R2 |
|---|---|---|---|
| L9 | O | H | H |
| L10 | O | H | Methyl |
| L11 | O | Methyl | H |
| L12 | O | Methyl | Methyl |
| L13 | O | H | t-butyl |
| L14 | O | t-butyl | H |
| L15 | O | t-butyl | t-butyl |
| L16 | S | H | H |
| L17 | S | H | Methyl |
| L18 | S | Methyl | H |
| L19 | S | Methyl | Methyl |
| L20 | S | H | t-butyl |
| L21 | S | t-butyl | H |
| L22 | S | t-butyl | t-butyl |
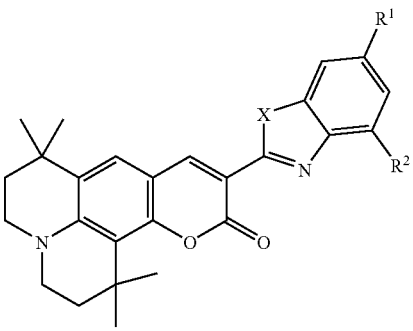
|  | X | R1 | R2 |
|---|---|---|---|
| L23 | O | H | H |
| L24 | O | H | Methyl |

-continued
| | | | |
|---|---|---|---|
| L25 | O | Methyl | H |
| L26 | O | Methyl | Methyl |
| L27 | O | H | t-butyl |
| L28 | O | t-butyl | H |
| L29 | O | t-butyl | t-butyl |
| L30 | S | H | H |
| L31 | S | H | Methyl |
| L32 | S | Methyl | H |
| L33 | S | Methyl | Methyl |
| L34 | S | H | t-butyl |
| L35 | S | t-butyl | H |
| L36 | S | t-butyl | t-butyl |
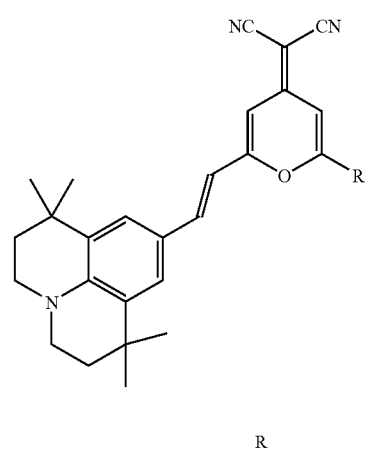
R
| | |
|---|---|
| L37 | phenyl |
| L38 | methyl |
| L39 | t-butyl |
| L40 | mesityl |
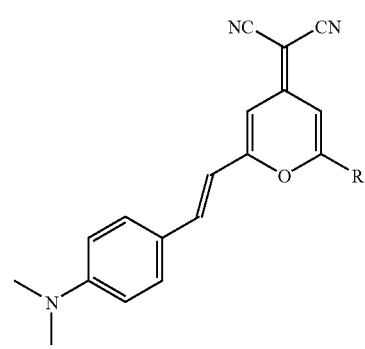
R
| | |
|---|---|
| L41 | phenyl |
| L42 | methyl |
| L43 | t-butyl |
| L44 | mesityl |
-continued
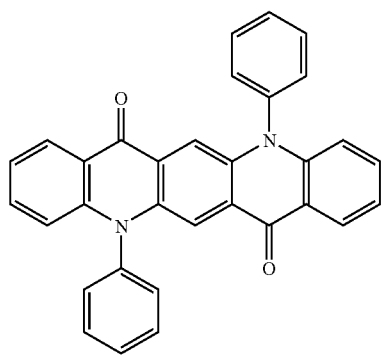
L45
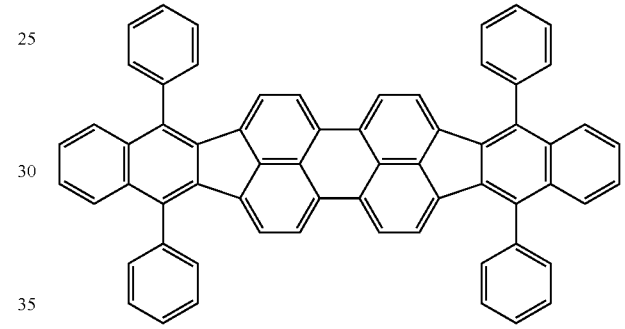
L46
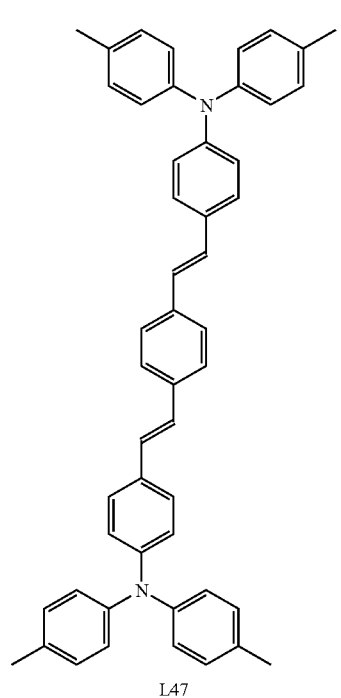
L47

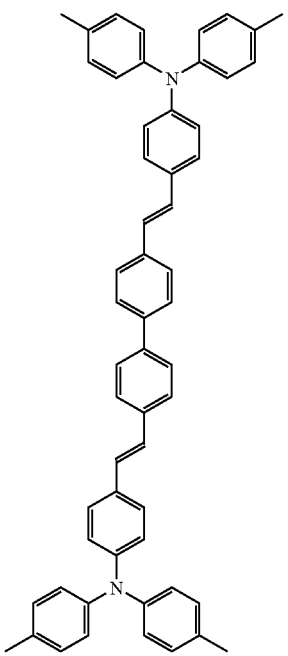

L48

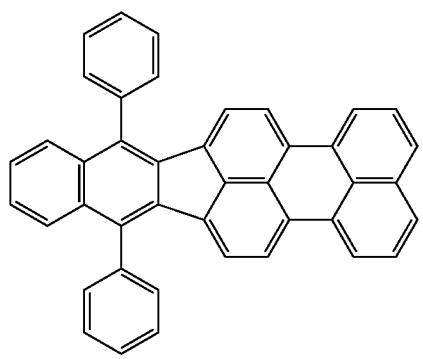

L49

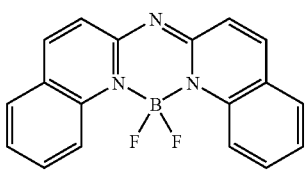

L50

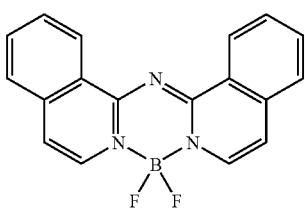

L51

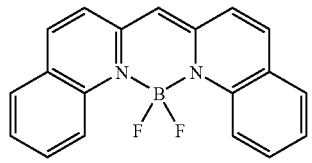

L52

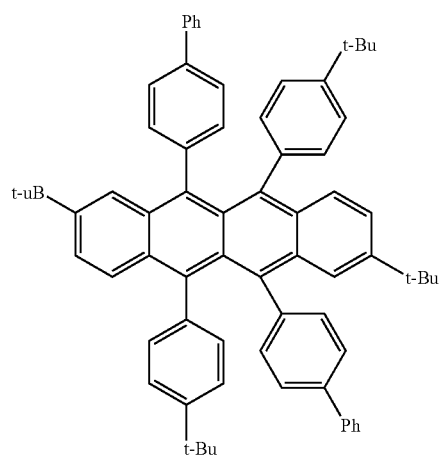

L53

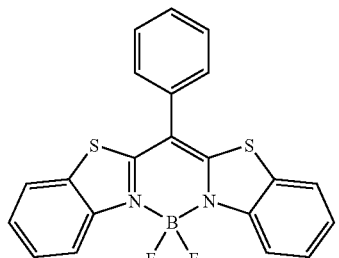

L54

In addition to the light-emitting materials of this invention, light-emitting phosphorescent materials may be used in the EL device. For convenience, the phosphorescent complex guest material may be referred to herein as a phosphorescent material. The phosphorescent material typically includes one or more ligands, for example monoanionic ligands that can be coordinated to a metal through an $sp^2$ carbon and a heteroatom. Conveniently, the ligand can be phenylpyridine (ppy) or derivatives or analogs thereof. Examples of some useful phosphorescent organometallic materials include tris(2-phenylpyridinato-N,$C^{2'}$)iridium(III), bis(2-phenylpyridinato-N,$C^{2'}$)iridium(III)(acetylacetonate), and bis(2-phenylpyridinato-N,$C^{2'}$)platinum(II). Usefully, many phosphorescent organometallic materials emit in the green region of the spectrum, that is, with a maximum emission in the range of 510 to 570 nm.

Phosphorescent materials may be used singly or in combinations other phosphorescent materials, either in the same or different layers. Phosphorescent materials and suitable hosts are described in WO 00/57676, WO 00/70655, WO 01/41512 A1, WO 02/15645 A1, US 2003/0017361 A1, WO 01/93642 A1, WO 01/39234 A2, U.S. Pat. No. 6,458,475 B1, WO 02/071813 A1, U.S. Pat. No. 6,573,651 B2, US 2002/

0197511 A1, WO 02/074015 A2, U.S. Pat. No. 6,451,455 B1, U.S. 2003/0072964 A1, US 2003/0068528 A1, U.S. Pat. Nos. 6,413,656 B1, 6,515,298 B2, 6,451,415 B1, 6,097,147, US 2003/0124381 A1, US 2003/0059646 A1, US 2003/0054198 A1, EP 1 239 526 A2, EP 1 238 981 A2, EP 1 244 155 A2, US 2002/0100906 A1, US 2003/0068526 A1, US 2003/0068535 A1, JP 2003073387A, JP 2003 073388A, US 2003/0141809 A1, US 2003/0040627 A1, JP 2003059667A, JP 2003073665A, and US 2002/0121638 A1.

The emission wavelengths of cyclometallated IR(III) complexes of the type $IrL_3$ and $IrL_2L'$, such as the green-emitting fac-tris(2-phenylpyridinato-N,$C^{2'}$)iridium(III) and bis(2-phenylpyridinato-N,$C^{2'}$)iridium(III)(acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,$C^{3'}$)iridium(III)(acetylacetonate) and tris(2-phenylisoquinolinato-N,C)iridium(III). A blue-emitting example is bis(2-(4,6-difluorophenyl)-pyridinato-N,$C^{2'}$)iridium(III)(picolinate).

Red electrophosphorescence has been reported, using bis (2-(2'-benzo[4,5-a]thienyl)pyridinato-N, $C^3$) iridium (acetylacetonate) [$Btp_2Ir(acac)$] as the phosphorescent material (C. Adachi, S. Lamansky, M. A. Baldo, R. C. Kwong, M. E. Thompson, and S. R. Forrest, App. Phys. Lett., 78, 1622-1624 (2001)).

Other important phosphorescent materials include cyclometallated Pt(II) complexes such as cis-bis(2-phenylpyridinato-N,$C^{2'}$)platinum(II), cis-bis(2-(2'-thienyl)pyridinato-N,$C^{3'}$) platinum(II), cis-bis(2-(2'-thienyl)quinolinato-N,$C^{5'}$) platinum(II), or (2-(4,6-difluorophenyl)pyridinato-N,$C^{2'}$) platinum (II) (acetylacetonate). Pt (II) porphyrin complexes such as 2,3,7,8,12,13,17,18-octaethyl-21H, 23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al., Appl. Phys. Lett., 65, 2124 (1994)).

Suitable host materials for phosphorescent materials should be selected so that transfer of a triplet exciton can occur efficiently from the host material to the phosphorescent material but cannot occur efficiently from the phosphorescent material to the host material. Therefore, it is highly desirable that the triplet energy of the phosphorescent material be lower than the triplet energy of the host. Generally speaking, a large triplet energy implies a large optical bandgap. However, the band gap of the host should not be chosen so large as to cause an unacceptable barrier to injection of charge carriers into the light-emitting layer and an unacceptable increase in the drive voltage of the OLED. Suitable host materials are described in WO 00/70655 A2; 01/39234 A2; 01/93642 A1; 02/074015 A2; 02/15645 A1, and US 20020117662. Suitable hosts include certain aryl amines, triazoles, indoles and carbazole compounds. Examples of desirable hosts are 4,4'-N,N'-dicarbazole-biphenyl, otherwise known as 4,4'-bis(carbazol-9-yl) biphenyl or CBP; 4,4'-N,N'-dicarbazole-2,2'-dimethyl-biphenyl, otherwise known as 2,2'-dimethyl-4,4'-bis(carbazol-9-yl)biphenyl or CDBP; 1,3-bis(N,N'-dicarbazole)benzene, otherwise known as 1,3-bis(carbazol-9-yl)benzene, and poly (N-vinylcarbazole), including their derivatives.

Desirable host materials are capable of forming a continuous film.

Hole-Blocking Layer (HBL)

In addition to suitable hosts, an OLED device employing a phosphorescent material often requires at least one hole-blocking layer placed between the electron-transporting layer 111 and the light-emitting layer 109 to help confine the excitons and recombination events to the light-emitting layer comprising the host and phosphorescent material. In this case, there should be an energy barrier for hole migration from the host into the hole-blocking layer, while electrons should pass readily from the hole-blocking layer into the light-emitting layer comprising a host and a phosphorescent material. The first requirement entails that the ionization potential of the hole-blocking layer be larger than that of the light-emitting layer 109, desirably by 0.2 eV or more. The second requirement entails that the electron affinity of the hole-blocking layer not greatly exceed that of the light-emitting layer 109, and desirably be either less than that of light-emitting layer or not exceed that of the light-emitting layer by more than about 0.2 eV.

When used with an electron-transporting layer whose characteristic luminescence is green, such as an Alq-containing electron-transporting layer as described below, the requirements concerning the energies of the highest occupied molecular orbital (HOMO) and lowest unoccupied molecular orbital (LUMO) of the material of the hole-blocking layer frequently result in a characteristic luminescence of the hole-blocking layer at shorter wavelengths than that of the electron-transporting layer, such as blue, violet, or ultraviolet luminescence. Thus, it is desirable that the characteristic luminescence of the material of a hole-blocking layer be blue, violet, or ultraviolet. It is further desirable, but not absolutely required, that the triplet energy of the hole-blocking material be greater than that of the phosphorescent material. Suitable hole-blocking materials are described in WO 00/70655A2 and WO 01/93642 A1. Two examples of useful hole-blocking materials are bathocuproine (BCP) and bis(2-methyl-8-quinolinolato)(4-phenylphenolato)aluminum(III) (BAlq). The characteristic luminescence of BCP is in the ultraviolet, and that of BAlq is blue. Metal complexes other than BAlq are also known to block holes and excitons as described in US 20030068528. In addition, US 20030175553 A1 describes the use of fac-tris(1-phenylpyrazolato-N,$C^{2'}$)iridium(III) (Irppz) for this purpose.

When a hole-blocking layer is used, its thickness can be between 2 and 100 nm and suitably between 5 and 10 nm.

Electron-Transporting Layer (ETL)

Desirable thin film-forming materials for use in forming the electron-transporting layer 111 of the organic EL devices of this invention are metal-chelated oxinoid compounds, including chelates of oxine itself (also commonly referred to as 8-quinolinol or 8-hydroxyquinoline). Such compounds help to inject and transport electrons, exhibit high levels of performance, and are readily fabricated in the form of thin films. Exemplary of contemplated oxinoid compounds are those satisfying structural formula (E), previously described.

Other electron-transporting materials suitable for use in the electron-transporting layer 111 include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials.

If both a hole-blocking layer and an electron-transporting layer 111 are used, electrons should pass readily from the electron-transporting layer 111 into the hole-blocking layer. Therefore, the electron affinity of the electron-transporting layer 111 should not greatly exceed that of the hole-blocking layer. Desirably, the electron affinity of the electron-transporting layer should be less than that of the hole-blocking layer or not exceed it by more than about 0.2 eV.

If an electron-transporting layer is used, its thickness may be between 2 and 100 nm and suitably between 5 and 20 nm.

Other Useful Organic Layers and Device Architecture

In some instances, layers 109 through 111 can optionally be collapsed into a single layer that serves the function of supporting both light emission and electron transportation. The hole-blocking layer, when present, and layer 111 may also be collapsed into a single layer that functions to block holes or excitons, and supports electron transport. It also known in the art that emitting materials may be included in the hole-transporting layer 107. In that case, the hole-transporting material may serve as a host. Multiple emitting materials may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, US 20020025419, EP 1 182 244, U.S. Pat. Nos. 5,683,823, 5,503,910, 5,405,709, and 5,283,182 and can be equipped with a suitable filter arrangement to produce a color emission.

This invention may be used in so-called stacked device architecture, for example, as taught in U.S. Pat. Nos. 5,703,436 and 6,337,492.

Deposition of Organic Layers

The organic materials mentioned above are suitably deposited by any means suitable for the form of the organic materials. In the case of small molecules, they are conveniently deposited through sublimation or evaporation, but can be deposited by other means such as coating from a solvent together with an optional binder to improve film formation. If the material is a polymer, solvent deposition is usually preferred. The material to be deposited by sublimation or evaporation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) or an inkjet method (U.S. Pat. No. 6,066,357).

One desirable method for depositing the materials of the present invention is described in US 2004/0255857 and U.S. Ser. No. 10/945,941 where different source evaporators are used to evaporate each of the materials of the present invention. A second desirable method involves the use of flash evaporation where materials are metered along a material feed path in which the material feed path is temperature controlled. Such a method is described in the following co-assigned patent applications: U.S. Ser. Nos. 10/784,585; 10/805,980; 10/945,940; 10/945,941; 11/050,924; and 11/050,934. Using this second method, each material may be evaporated using different source evaporators or the solid materials may be mixed prior to evaporation using the same source evaporator.

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as $SiO_x$, Teflon, and alternating inorganic/polymeric layers are known in the art for encapsulation. Any of these methods of sealing or encapsulation and desiccation can be used with the EL devices constructed according to the present invention.

Optical Optimization

OLED devices of this invention can employ various well-known optical effects in order to enhance their emissive properties if desired. This includes optimizing layer thicknesses to yield maximum light transmission, providing dielectric mirror structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings may be specifically provided over the EL device or as part of the EL device.

Embodiments of the invention may provide advantageous features such as higher luminous yield, lower drive voltage, higher power efficiency, greater operational stability, and reduced variation of chromaticity and/or luminous yield with current density. Also, the embodiments may be used in a wider range of concentrations leading to improved manufacturability. Embodiments of the compounds useful in the invention can provide a wide range of hues, especially blue and blue-green. They are useful in the emission of white light (directly or through filters to provide multicolor displays). Embodiments of the invention can also provide an area lighting device.

The invention and its advantages can be better appreciated by the following examples.

SYNTHETIC EXAMPLES

Preparation of 4-Bromo-4'-(di-tolylamino)stilbene

Diethyl-(4-bromobenzyl)phosphonate (35.9 g, 0.117 mol), 4-(Di-p-tolylamino)benzaldehyde (32 g, 0.106 mol) and sodium methoxide (7.5 g, 0.138 mol) were stirred in 200 mL of dry dimethylformamide at ambient temperature for 2 hours, then at 85 C for 2 hours. The reaction was cooled to 25 C, then poured into 450 mL of a 5% wt/wt aqueous HCl solution. The precipitated material was triturated with hexanes to produce a yellow solid which was recrystallized from a toluene-ethanol mixture to yield 28.3 g of product. The analytical data were consistent with the structure.

Preparation of 4-(Di-p-tolylamino)phenylboronic Acid

A solution of 4-Bromo-4'-(di-p-tolylamino)benzene (25 g, 0.071 mol) in 60 mL dry tetrahydrofuran was cooled to −78 C under nitrogen. Butyllithium (0.078 mol) was added to the reaction as a 1.6M solution in hexanes. After the reaction stirred at low temperature for 1.5 hours, triethylborate (11.4 g, 0.078 mol) was added and the reaction was allowed to warm to 25 C. The reaction was diluted with diethyl ether and the organic layer was washed with water, dried, filtered and concentrated. The residue was triturated with hexanes, then filtered to yield the 17.5 g of the boronic acid. All analytical data were consistent with the structure.

Preparation of Compound (I-1)

4-(Ditolylamino)phenylboronic acid (3.0 mmol) and 1-bromo-4-(4-ditolylaminostyryl)benzene (3.5 mmol) were combined in a mixture of degassed toluene and dichlorobis(triphenylphosphine)palladium II. Aqueous sodium carbonate (6.0 mmol) was added, and the reaction was heated to 100 C for 12 hours. The mixture was diluted with toluene and filtered. The filtrate was washed with water, and the organic layer was then dried and concentrated. The concentrate was triturated with hexanes, and the resulting solid was recrystallized from ethanol-hexanes to produce a yellow solid. All analytical data was consistent with the assigned structure.

Comparative Compounds

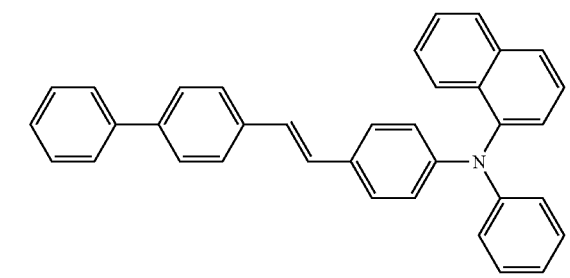

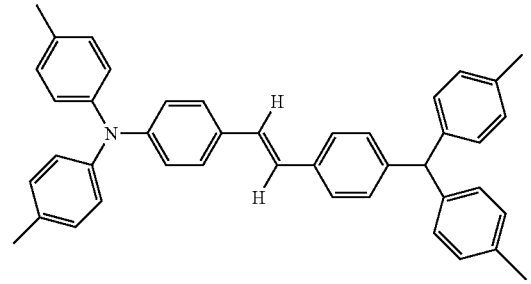

-continued

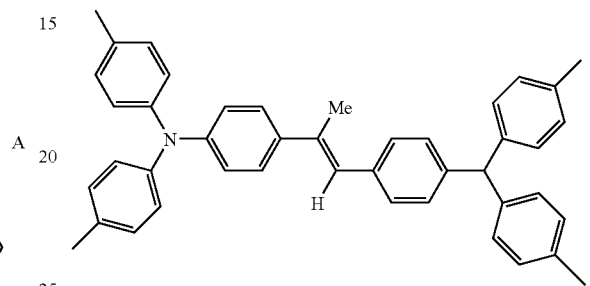

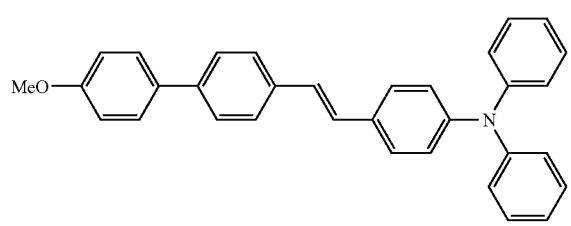

Example of Maximum Emission and Luminance Efficiency

The emission spectra for the compounds in the Table below were obtained at room temperature in ethyl acetate solution at concentrations of $10^{-5}$ to $10^{-6}$ M and expressed as quanta per unit time per unit wavelength interval against wavelength. A fluorescence procedure is well known to those skilled in the art (see, for example, C. A. Parker and W. T. Rees, *Analyst*, 85, 587 (1960)). The maximum of emission spectra is defined as the wavelength corresponding to the highest point of such spectrum. The results are shown in the following table.

| Example | Type | Compound | Wavelength of Maximum Emission (nm) | Quantum Yield. |
|---|---|---|---|---|
| 1 | Comparative | E | 438 | 0.907 |
| 2 | Comparative | G | 413 | 0.371 |
| 3 | Inventive | I-1 | 463 | 0.984 |

In order to be efficient, it is highly desirable that light-emitting materials considered for use in an OLED device have as high a quantum yield as possible. As can be seen from the Table above, the quantum yield of Comparative Compound G, having a stryl group with a tri-substituted double bond is much lower than that for Comparative Compound E, which has only two substituents on the double bond. Inventive Compound I-1 has the highest quantum yield in the series.

Comparative Device Example 1

A comparative EL device was constructed in the following manner:

1. A glass substrate coated with an 20 nm layer of indium-tin oxide (ITO) as the anode is sequentially ultrasonicated in a commercial detergent, rinsed in deionized water, degreased in toluene vapor and exposed to oxygen plasma for about 1 min.

2. Over the ITO is deposited a 1 nm fluorocarbon (CFx) hole-injecting layer (HIL) by plasma-assisted deposition of $CHF_3$ as described in U.S. Pat. No. 6,208,075.
3. The above-prepared substrate was further treated by vacuum-depositing a 75 nm layer of 4,4'-bis[N-(1-naphthyl)-N-phenylamino]biphenyl as a hole-transporting layer (HTL).
4. A coating of 20 nm of 9-(2-naphthyl)-10-(4-biphenyl) anthracene as a host and 3% (0.6 nm eq.) of (Compound L47, above) as a blue dopant was evaporatively deposited on the above substrate to form a blue-light-emitting layer (blue EML).
5. A 35 nm electron-transporting layer (ETL) of tris(8-quinolinolato)aluminum (III) (ALQ) was vacuum-deposited onto the substrate at a coating station that included a heated tantalum boat source.
6. A 220 nm layer of a 10:1 volume ratio of Mg and Ag was evaporatively deposited onto the substrate, to form a cathode layer.

The above sequence completes the deposition of the EL device. The device is then hermetically packaged in a dry glove box for protection against ambient environment.

Comparative Device Example 2

A comparative EL was constructed following the steps above, except that Step 4 is as follows:
4. A coating of 20 nm of 9-(2-naphthyl)-10-(4-biphenyl) anthracene as a host and 3% (0.6 nm eq.) (Compound L2, above) as a blue dopant was evaporatively deposited on the above substrate to form a blue-light-emitting layer (blue EML).

Comparative Device Example 3

A comparative EL was constructed following the steps above, except that Step 4 is as follows:
4. A coating of 20 nm of 9-(2-naphthyl)-10-(4-biphenyl) anthracene as a host and 3% (0.6 nm eq.) (Comparative Compound A) as a blue dopant was evaporatively deposited on the above substrate to form a blue-light-emitting layer (blue EML).

Comparative Device Example 4

A comparative EL was constructed following the steps above, except that Step 4 is as follows:
4. A coating of 20 nm of 9-(2-naphthyl)-10-(4-biphenyl) anthracene as a host and 6% (1.2 nm eq.) (Comparative Compound B) as a blue dopant was evaporatively deposited on the above substrate to form a blue-light-emitting layer (blue EML).

Inventive Device Example 1

An EL device satisfying the requirements of the invention was constructed following the steps for Comparative Example 1 above, except that Step 4 is as follows:
4. A coating of 20 nm of 9-(2-naphthyl)-10-(4-biphenyl) anthracene as a host and 4% (0.8 nm eq.) (Compound I-1) as a blue dopant was evaporatively deposited on the above substrate to form a blue-light-emitting layer (blue EML).

Inventive Device Example 2

An EL device satisfying the requirements of the invention was constructed following the steps for Comparative Example 1 above, except that Step 4 is as follows:
4. A coating of 20 nm of 9-(2-naphthyl)-10-(4-biphenyl) anthracene as a host and 6% (1.2 nm eq.) (Compound I-1) as a blue dopant was evaporatively deposited on the above substrate to form a blue-light-emitting layer (blue EML).

A current of 20 mA/cm2 was applied across the electrodes of each device. The emission spectrum was measured, enabling the device characteristics in Tables 1 and 2 to be calculated. The relative luminous yield is defined as the luminous yield of the inventive example device, in cd/A, divided by the luminous yield, in cd/A, of one of the comparative example devices. The relative external efficiency is defined as the external efficiency of the prophetic example device, in W/A, divided by the external efficiency, in W/A, of one of the comparative example devices. Tables 1 and 2 below show the results.

TABLE 1

|  | Comparative Example 1 | Inventive Example 1 Relative to Comp. Ex. 1 | Comparative Example 2 | Inventive Example 2 Relative to Comp. Ex. 2 |
| --- | --- | --- | --- | --- |
| 1931 CIE x | 0.16 | 0.15 | 0.15 | 0.15 |
| 1931 CIE y | 0.30 | 0.17 | 0.20 | 0.20 |
| Relative External Efficiency (W/A) | 1.00 | 1.01 | 1.00 | 1.71 |
| Relative Luminous Yield (cd/A) | 1.00 | 0.69 | 1.00 | 1.77 |

TABLE 2

|  | Comparative Example 3 | Comparative Example 4 | Inventive Example 1 Relative to Comp. Ex. 3 | Inventive Example 1 Relative to Comp. Ex. 4 |
| --- | --- | --- | --- | --- |
| 1931 CIE x | 0.16 | 0.16 | 0.15 | 0.15 |
| 1931 CIE y | 0.14 | 0.17 | 0.17 | 0.17 |
| Relative External Efficiency (W/A) | 1.00 | 1.00 | 2.41 | 1.71 |
| Relative Luminous Yield (cd/A) | 1.00 | 1.00 | 2.89 | 1.75 |

As shown in Table 1, the inventive dopant material results in blue OLED devices with a better blue chromaticity than the reference dopant used in Comparative Example 1, with a comparable external efficiency. The inventive dopant material results in blue OLED devices with similar blue chromaticity to the reference dopant used in Comparative Example 2 with significantly higher external efficiency & luminous yield.

As shown in Table 2, the inventive dopant material results in blue devices with similar blue chromaticity to the dopants used in Comparative Examples 3 and 4. However, the inventive dopant material results in blue OLED devices with significantly higher external efficiency & luminous yield.

Comparative Device Example 5

A comparative EL device was constructed in the following manner:

1. A glass substrate coated with an 20 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of $CHF_3$ as described in U.S. Pat. No. 6,208,075.
3. The above-prepared substrate was further treated by vacuum-depositing a 95 nm layer of 4,4'-bis[N-(1-naphthyl)-N-phenylamino]biphenyl as a hole-transporting layer (HTL).
4. A coating of 40 nm of 9-(2-naphthyl)-10-(4-biphenyl) anthracene as a host and 6% (2.4 nm eq.) (Comparative Compound C, above) as a blue dopant was evaporatively deposited on the above substrate to form a blue-light-emitting layer (blue EML).
5. A 15 nm electron-transporting layer (ETL) of tris(8-quinolinolato)aluminum (III) (ALQ) was vacuum-deposited onto the substrate at a coating station that included a heated graphite boat source.
6. A 1.0 nm layer of lithium fluoride was evaporatively deposited onto the substrate, followed by a 200 nm layer of aluminum, to form a cathode layer.

The above sequence completes the deposition of the EL device. The device is then hermetically packaged in a dry glove box for protection against ambient environment.

Comparative Device Example 6

An EL device satisfying the requirements of the invention was constructed following the steps above, except that Step 4 is as follows:

4. A coating of 40 nm of 9-(2-naphthyl)-10-(4-biphenyl) anthracene as a host and 6% (2.4 nm eq.) (Comparative Compound D, above) as a blue dopant was evaporatively deposited on the above substrate to form a blue-light-emitting layer (blue EML).

Inventive Device Example 3

An EL device satisfying the requirements of the invention was constructed following the steps for Comparative Example 5 above, except that Step 4 is as follows:

4. A coating of 40 nm of 9-(2-naphthyl)-10-(4-biphenyl) anthracene as a host and 3% (1.6 nm eq.) (Compound I-1) as a blue dopant was evaporatively deposited on the above substrate to form a blue-light-emitting layer (blue EML).

A current of 20 mA/cm$^2$ was applied across the electrodes of each device. The emission spectrum was measured, enabling the device characteristics in Table 3 to be calculated. The relative luminous yield is defined as the luminous yield of the prophetic example device, in cd/A, divided by the luminous yield, in cd/A, of one of the comparative example devices. The relative external efficiency is defined as the external efficiency of the prophetic example device, in W/A, divided by the external efficiency, in W/A, of one of the comparative example devices. Table 3 below shows the results.

TABLE 3

| | Comparative Example 5 | Comparative Example 6 | Inventive Example 3 Relative to Comp. Ex. 5 | Inventive Example 3 Relative to Comp. Ex. 6 |
| --- | --- | --- | --- | --- |
| 1931 CIE x | 0.18 | 0.18 | 0.15 | 0.15 |
| 1931 CIE y | 0.19 | 0.19 | 0.20 | 0.20 |
| Relative External Efficiency (W/A) | 1.00 | 1.00 | 2.00 | 2.00 |
| Relative Luminous Yield (cd/A) | 1.00 | 1.00 | 1.98 | 1.87 |

As shown in Table 3, the inventive dopant material results in blue devices with similar blue chromaticity to the dopants used in Comparative Examples 5 and 6. However, the inventive dopant material results in blue OLED devices with twice the external efficiency & luminous yield.

Comparative Device Example 7

A comparative EL device was constructed in the following manner:

1. A glass substrate coated with an 85 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of $CHF_3$ as described in U.S. Pat. No. 6,208,075.
3. The above-prepared substrate was further treated by vacuum-depositing a 75 nm layer of 4,4'-bis[N-(1-naphthyl)-N-phenylamino]biphenyl as a hole-transporting layer (HTL).
4. A coating of 40 nm of 9-(2-naphthyl)-10-(4-biphenyl) anthracene as a host and 4% (1.6 nm eq.) (Compound L2, above) as a blue dopant was evaporatively deposited on the above substrate to form a blue-light-emitting layer (blue EML).
4. A 10 nm electron-transporting layer (ETL) of tris(8-quinolinolato)aluminum (III) (ALQ) was vacuum-deposited onto the substrate at a coating station that included a heated graphite boat source.
5. A 1.0 nm layer of lithium fluoride was evaporatively deposited onto the substrate, followed by a 100 nm layer of aluminum, to form a cathode layer.

The above sequence completes the deposition of the EL device. The device is then hermetically packaged in a dry glove box for protection against ambient environment.

Inventive Device Example 4

An EL device satisfying the requirements of the invention was constructed following the steps above, except that Step 4 is as follows:

4. A coating of 40 nm of 9-(2-naphthyl)-10-(4-biphenyl) anthracene as a host and 4% (1.6 nm eq.) (Compound Formula I-1) as a blue dopant was evaporatively deposited on the above substrate to form a blue-light-emitting layer (blue EML).

A current of 20 mA/cm$^2$ was applied across the electrodes of each device. The emission spectrum was measured, enabling the device characteristics in Table 4 to be calculated.

The relative luminous yield is defined as the luminous yield of the prophetic example device, in cd/A, divided by the luminous yield, in cd/A, of Comparative Example 7. The relative external efficiency is defined as the external efficiency of the Inventive example device, in W/A, divided by the external efficiency, in W/A, of Comparative Example 7. For lifetime, the intensity was monitored as a function of time from an initial luminance of 1000 cd/m$^2$. The relative lifetime is defined as the time to half-luminance intensity of the inventive example device, in hours, divided by the time to half-luminance intensity of Comparative Example 7. Table 4 below shows the results.

TABLE 4

|  | Comparative Example 7 | Inventive Example 4 |
|---|---|---|
| 1931 CIE x | 0.14 | 0.15 |
| 1931 CIE y | 0.23 | 0.23 |
| Relative External Efficiency (W/A) | 1.00 | 1.63 |
| Relative Luminous Yield (cd/A) | 1.00 | 1.68 |
| Relative Lifetime | 1.00 | 2.00 |

Figure 2:
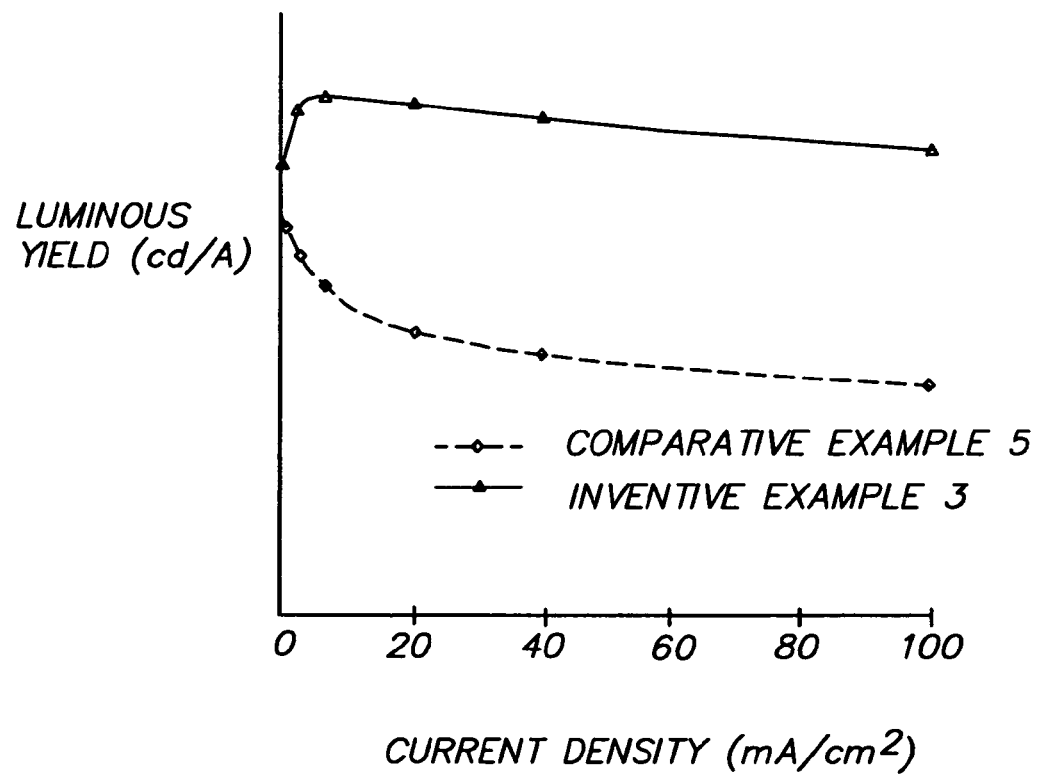
FIG. 2 is a graph of the results of Example 4 showing that the luminous yield does not vary with current density.

Devices prepared according to Inventive Example 4 exhibited significantly higher luminous yield & external efficiency than the reference device, Comparative Example 7, with a conventional blue dopant. Inventive Example 4 also demonstrated twice the lifetime of the reference device, from an initial luminance of 1000 cd/m$^2$. An additional advantage of the inventive dopant material is that the luminous yield of the resultant blue device does not vary with current density as much as the device using the comparative dopant material, as shown in FIG. 2.

Comparative Device Example 8

An EL device satisfying the requirements of the invention was constructed in the following manner:
1. A glass substrate coated with an 85 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of CHF$_3$ as described in U.S. Pat. No. 6,208,075.
3. The above-prepared substrate was further treated by vacuum-depositing a 140 nm layer of 4,4'-bis[N-(1-naphthyl)-N-phenylamino]biphenyl as a hole-transporting layer (HTL).
4. A layer comprised of 68% (21 nm eq.) of 4,4'-bis[N-(1-naphthyl)-N-phenylamino]biphenyl, 29% (9 nm eq.) of 9-(2-naphthyl)-10-(4-biphenyl)anthracene, and 3% (0.9 nm eq.) of L53 was evaporatively deposited on the above substrate to form a yellow-light-emitting layer (yellow EML).
5. A layer comprised of 42 nm of 9-(2-naphthyl)-10-(4-biphenyl)anthracene, 3 nm of 4,4'-bis[N-(1-naphthyl)-N-phenylamino]biphenyl, and 1.1% (0.45 nm eq.) of L2 as a blue dopant was evaporatively deposited on the above substrate to form a blue-light-emitting layer (blue EML).
6. A 10 nm electron-transporting layer (ETL) of tris(8-quinolinolato)aluminum (III) (ALQ) was vacuum-deposited onto the substrate at a coating station that included a heated graphite boat source.
7. A 1.0 nm layer of lithium fluoride was evaporatively deposited onto the substrate, followed by a 100 nm layer of aluminum, to form a cathode layer.

The above sequence completes the deposition of the EL device. The device is then hermetically packaged in a dry glove box for protection against ambient environment.

Inventive Device Example 5

An EL device satisfying the requirements of the invention was constructed following the steps above, except that Step 5 is as follows:
5. A coating of 45 nm of 9-(2-naphthyl)-10-(4-biphenyl) anthracene as a host and 2% (0.9 nm eq.) (Compound Formula I-1) as a blue dopant was evaporatively deposited on the above substrate to form a blue-light-emitting layer (blue EML).

Inventive Device Example 6

An EL device satisfying the requirements of the invention was constructed following the steps for Comparative Example 7 above, except that Step 5 is as follows:
5. A coating of 45 nm of 9-(2-naphthyl)-10-(4-biphenyl) anthracene as a host and 4% (1.8 nm eq.) (Compound Formula I-1) as a blue dopant was evaporatively deposited on the above substrate to form a blue-light-emitting layer (blue EML).

A current of 20 mA/cm$^2$ was applied across the electrodes of each device. The emission spectrum was measured, enabling the device characteristics in Table 4 to be calculated. The term "Delta CIE" is a measure of how the chromaticity of a device changes with the current applied across the electrodes. Ideally, the chromaticity would not change with applied current and "Delta CIE" would be zero. The term "Delta CIE" is defined as follows:

$$\text{Delta } CIE = \sqrt{(\text{Delta}CIEx)^2 + (\text{Delta}CIEy)^2}$$

$$\text{Delta}CIEx = (1931\ CIEx\ @\ 100\ \text{mA/cm}^2) - (1931\ CIEx\ @\ 0.5\ \text{mA/cm}^2)$$

$$\text{Delta}CIEy = (1931\ CIEy\ @\ 100\ \text{mA/cm}^2) - (1931\ CIEY\ @ 0.5\ \text{mA/cm}^2)$$

As shown in Table 5, very efficient white OLED devices can be prepared using this inventive dopant material. By altering the concentration of the blue dopant material, the chromaticity of the white emission can be altered. The luminous yield of inventive white OLED devices was greater than that of the comparative. An additional advantage of the inventive blue dopant material is that the resultant white OLED devices have a smaller Delta CIE than those incorporating the comparative blue dopant material.

TABLE 5

|  | Comparative Example 8 | Inventive Example 5 | Inventive Example 6 |
|---|---|---|---|
| 1931 CIE x | 0.32 | 0.34 | 0.28 |
| 1931 CIE y | 0.33 | 0.35 | 0.30 |
| External Efficiency (W/A) | 0.12 | 0.12 | 0.14 |
| Luminous Yield (cd/A) | 11.28 | 11.94 | 11.72 |
| Delta CIE | 0.045 | 0.018 | 0.034 |

Comparative Device Example 9

A comparative EL device was constructed in the following manner:
1. A glass substrate coated with an 85 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of $CHF_3$ as described in U.S. Pat. No. 6,208,075.
3. The above-prepared substrate was further treated by vacuum-depositing a 75 nm layer of 4,4'-bis[N-(1-naphthyl)-N-phenylamino]biphenyl as a hole-transporting layer (HTL).
4. A coating of 20 nm of 9-(2-naphthyl)-10-(4-biphenyl)anthracene as a host and 3% of Compound L47 as a blue dopant was evaporatively deposited on the above substrate to form a blue-light-emitting layer (blue EML).
5. A 35 nm electron-transporting layer (ETL) of tris(8-quinolinolato)aluminum (III) (ALQ) was vacuum-deposited onto the substrate at a coating station that included a heated graphite boat source.
6. A 0.5 nm layer of lithium fluoride was evaporatively deposited onto the substrate, followed by a 100 nm layer of aluminum, to form a cathode layer.

The above sequence completes the deposition of the EL device. The device is then hermetically packaged in a dry glove box for protection against ambient environment.

Inventive Device Example 7

An EL device satisfying the requirements of the invention was constructed following the steps in Comparative Example 9, except that the blue dopant L47 was replaced with I-30 at a level of 4%.

Inventive Device Example 8

An EL device satisfying the requirements of the invention was constructed following the steps in Inventive Example 7, except that the blue dopant I-30 was used at a level of 6%.

Comparative device example 9 and inventive devices 7 and 8 were evaluated by applying a current of 20 mA/cm$^2$ across the electrodes of each device. The emission spectrum was measured, enabling the device characteristics in Table 6 to be calculated. The relative luminous yield is defined as the luminous yield of the Inventive example devices, in cd/A, divided by the luminous yield, in cd/A, of Comparative Example 9. The relative external efficiency is defined as the external efficiency of the Inventive example devices, in W/A, divided by the external efficiency, in W/A, of Comparative Example 9. Table 6 below shows the results.

TABLE 6

|  | Comparative Example 9 | Inventive Example 7 | Inventive Example 8 |
| --- | --- | --- | --- |
| 1931 CIE x | 0.167 | 0.152 | 0.151 |
| 1931 CIE y | 0.350 | 0.186 | 0.195 |
| Relative External Efficiency (W/A) | 1.00 | 0.98 | 1.06 |
| Relative Luminous Yield (cd/A) | 1.00 | 0.63 | 0.71 |

As shown in Table 6, the inventive dopant material results in blue OLED devices with a better blue chromaticity than the device using the reference dopant material, Comparative Example 9, with a similar external efficiency.

Comparative Device Example 10

A comparative EL device was constructed in the following manner:
1. A glass substrate coated with an 85 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of $CHF_3$ as described in U.S. Pat. No. 6,208,075.
3. The above-prepared substrate was further treated by vacuum-depositing a 75 nm layer of 4,4'-bis[N-(1-naphthyl)-N-phenylamino]biphenyl as a hole-transporting layer (HTL).
4. A coating of 20 nm of 9-(2-naphthyl)-10-(4-biphenyl)anthracene as a host and 3% of Compound L47 as a blue dopant was evaporatively deposited on the above substrate to form a blue-light-emitting layer (blue EML).
5. A 35 nm electron-transporting layer (ETL) of tris(8-quinolinolato)aluminum (III) (ALQ) was vacuum-deposited onto the substrate at a coating station that included a heated graphite boat source.
6. A 0.5 nm layer of lithium fluoride was evaporatively deposited onto the substrate, followed by a 100 nm layer of aluminum, to form a cathode layer.

The above sequence completes the deposition of the EL device. The device is then hermetically packaged in a dry glove box for protection against ambient environment.

Inventive Device Example 9

An EL device satisfying the requirements of the invention was constructed following the steps in Comparative Example 10, except that the blue dopant L47 was replaced with I-31 at a level of 4%.

Inventive Device Example 10

An EL device satisfying the requirements of the invention was constructed following the steps in Inventive Example 9, except that the blue dopant I-31 was used at a level of 6%.

Comparative device example 10 and inventive devices 9 and 10 were evaluated by applying a current of 20 mA/cm$^2$ across the electrodes of each device. The emission spectrum was measured, enabling the device characteristics in Table 7 to be calculated. The relative luminous yield is defined as the luminous yield of the Inventive example devices, in cd/A, divided by the luminous yield, in cd/A, of Comparative Example 10. The relative external efficiency is defined as the external efficiency of the Inventive example devices, in W/A, divided by the external efficiency, in W/A, of Comparative Example 10. Table 7 below shows the results.

TABLE 7

|  | Comparative Example 10 | Inventive Example 9 | Inventive Example 10 |
| --- | --- | --- | --- |
| 1931 CIE x | 0.162 | 0.149 | 0.148 |
| 1931 CIE y | 0.341 | 0.181 | 0.193 |
| Relative External Efficiency (W/A) | 1.00 | 0.94 | 0.98 |
| Relative Luminous Yield (cd/A) | 1.00 | 0.61 | 0.67 |

As shown in Table 7, use of the inventive dopant material, in Examples 9 and 10, results in blue OLED devices with a better blue chromaticity than the device using the reference dopant, Comparative Example 10, with a similar external efficiency.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

PARTS LIST

101 Substrate
103 Anode
105 Hole-Injecting layer (HIL)
107 Hole-Transporting layer (HTL)
109 Light-Emitting layer (LEL)
111 Electron-Transporting layer (ETL)
113 Cathode
150 Power Source
160 Conductor

The invention claimed is:

1. An organic electroluminescent device comprising a cathode, an anode, and having therebetween a light-emitting layer comprising a non-polymeric emissive component represented by formula (I):

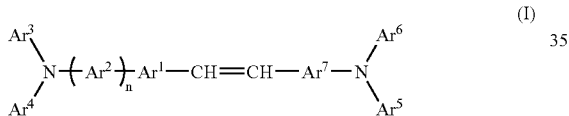

wherein:
Ar$^1$, each Ar$^2$, and Ar$^3$ through Ar$^6$ are independently selected aryl or heteroaryl groups, which may contain additional fused rings and provided that two aryl or heteroaryl rings may be joined;
wherein Ar$^7$ is a phenyl group; and
n is 1, 2 or 3.

2. The device of claim 1 wherein n is 1 or 2.

3. The device of claim 1 wherein Ar$^1$ through Ar$^6$ are hydrocarbons.

4. The device of claim 1 wherein at least one Ar$^2$ represents a heteroaryl group, which may contain additional fused rings.

5. The device of claim 1 wherein at least one Ar$^2$ represents a nitrogen containing heteroaryl group, which may contain additional fused rings.

6. The device of claim 1 wherein n is 1 or 2 and at least one of Ar$^2$ represents a pyridinediyl group, a quinolinediyl group, a benzothiazolediyl group, a benzoxazolediyl group, or a thiophenediyl group.

7. The device of claim 1 including, on the cathode side of said emitting layer, a further layer containing a first compound that has the lowest LUMO value of the compounds in the layer, the amount being greater than or equal to 10% by volume and less than 100% by volume of the layer; and at least one second compound that is a low voltage electron transport material, exhibiting a higher LUMO value than the first compound, the total amount of said compound(s) being less than or equal to 90% by volume and more than 0% by volume of the layer.

8. The device of claim 1 wherein Ar$^1$ through Ar$^6$ are independently selected from the group consisting of phenyl, and fused ring aryl groups.

9. The device of claim 1 wherein Ar$^1$ through Ar$^6$ are independently selected from the group consisting of phenyl, naphthyl, anthryl, and phenanthryl groups.

10. The device of claim 1 wherein the Ar$^1$-Ar$^6$ groups are selected to provide a compound with a sublimation temperature less than 204° C.

11. The device of claim 1 wherein at least one of the groups Ar$^3$, Ar$^4$, Ar$^5$, and Ar$^6$ is substituted with a non-aryl group.

12. The device of claim 11 wherein the non-aryl group is an alkyl group.

13. The device of claim 1 wherein the emissive component represented by formula (I) is present in an amount of from 2 to 6 wt% of the light emitting layer.

14. The device of claim 1 wherein there is additionally present in the light emitting layer a compound selected from a styryl, anthracene, perylene, naplithacene, or phenanthrene compound.

15. The device of claim 14 wherein the additional compound is an anthracene compound.

16. The device of claim 15 wherein the anthracene derivative is represented by general formula (V):

wherein
A$^1$ and A$^2$ each independently represent a substituted or unsubstituted anthracene group; and L represents a single bond or a linking group;
or by general formula (VI):

wherein
An represents a substituted or unsubstituted anthracene group; and
A$^3$ and A$^4$ each independently represent a substituted or unsubstituted condensed aromatic ring group or a substituted or unsubstituted non-condensed aromatic ring group; and An, A$^3$, and A$^4$ may be independently substituted with aryl, alkyl, cycloalkyl, alkoxy, aryloxy, aryl amine, nitro, cyano, ester, and halogen groups.

17. The device of claim 15 wherein the anthracene compound is selected from the group consisting of 9,10-di-(2-naphthyl)antbracene, 2-t-butyl-9,10-di-(2-naphthyl)antbracene and 9-(2-naphthyl)-10-(4-biphenyl)anthracene.

18. The device of claim 15 wherein the anthracene material comprises 70% to 99% by weight, of the layer.

19. The device of claim 1 wherein there are present in the light emitting layer a hole transporting material and an electron transport material.

20. The device of claim 19 wherein the additionally present hole transport material or the additionally present electron transport material is identical to a material in an adjacent layer of the device.

21. The device of claim 1 wherein white light is produced either directly or by using filters.

22. A compound represented by formula (III):

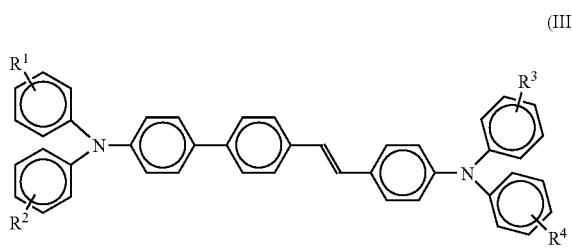

wherein $R^1$ through $R^4$ individually represents hydrogen or a substituent chosen from alkyl, alkoxy, amino, aryl, halogen, perfluoroalkyl, cyano, aryloxy or heterocyclic groups.

23. A display comprising the electroluminescent device of claim 1.

24. An area lighting device comprising the electroluminescent device of claim 1.

25. A process for emitting light comprising applying a potential across the device of claim 1.

26. An organic electroluminescent device of claim 1 wherein the layer containing emissive component represented by formula (I) is evaporatively deposited.

27. An organic electroluminescent device of claim 1 wherein $Ar^3$ through $A^7$ independently have substitu.ents chosen from hydrogen or alkyl, alkoxy, amino, aryl, halogen, periuoroalkyl, cyano, aryloxy or heterocyclic groups.

28. An organic electroluminescent device comprising a cathode, an anode, and having therebetween a light-emitting layer comprising a non-polymeric emissive component represented by formula (III):

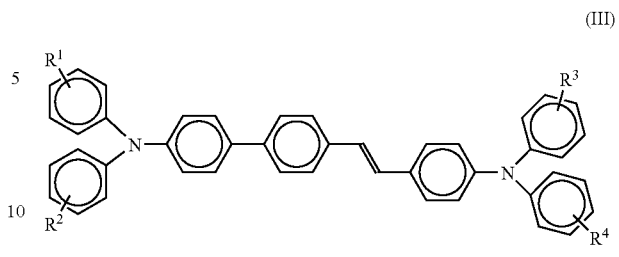

wherein $R^1$ through $R^4$ represent from 0 to 5 independently selected substituents that can be the same or different.

29. The device of claim 28 wherein at least one substituent is an alkyl, alkoxy, aryl, or aryloxy group.

30. An organic electroluminescent device comprising a cathode, an anode, and having therebetween a light-emitting layer comprising a non-polymeric emissive component represented by formula (III):

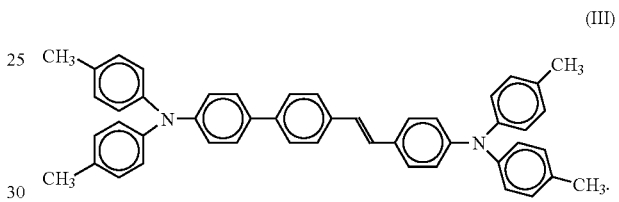

* * * * *